United States Patent
Mills et al.

(10) Patent No.: US 9,380,780 B2
(45) Date of Patent: *Jul. 5, 2016

(54) TRANSDERMAL VENOUS ACCESS LOCKING SOLUTIONS

(71) Applicant: Organic Medical Ventures, L.L.C., Norman, OK (US)

(72) Inventors: Stanley L. Mills, Goldsby, OK (US); Jacqueline L. Mills, Goldsby, OK (US); Robert D. Maurer, Omaha, NE (US); Gary L. Rayburn, Norman, OK (US); Marvin A. Cuchens, Ridgeland, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/698,345

(22) Filed: Apr. 28, 2015

(65) Prior Publication Data

US 2015/0245607 A1 Sep. 3, 2015

Related U.S. Application Data

(63) Continuation of application No. 13/222,221, filed on Aug. 31, 2011, now Pat. No. 9,072,296, which is a continuation-in-part of application No. 12/383,722, filed on Mar. 26, 2009, now abandoned.

(51) Int. Cl.

| | | |
|---|---|---|
| *A01N 37/44* | (2006.01) | |
| *A01N 37/00* | (2006.01) | |
| *A61K 31/20* | (2006.01) | |
| *A61K 31/727* | (2006.01) | |
| *A61K 45/06* | (2006.01) | |
| *A61L 29/14* | (2006.01) | |
| *A61L 29/16* | (2006.01) | |
| *A01N 37/02* | (2006.01) | |
| *A61L 29/08* | (2006.01) | |
| *A61M 25/00* | (2006.01) | |
| *A61M 39/02* | (2006.01) | |

(52) U.S. Cl.
CPC ............... *A01N 37/44* (2013.01); *A01N 37/00* (2013.01); *A01N 37/02* (2013.01); *A61K 31/20* (2013.01); *A61K 31/727* (2013.01); *A61K 45/06* (2013.01); *A61L 29/08* (2013.01); *A61L 29/14* (2013.01); *A61L 29/16* (2013.01); *A61L 2300/216* (2013.01); *A61L 2300/404* (2013.01); *A61L 2420/06* (2013.01); *A61M 25/0017* (2013.01); *A61M 25/0045* (2013.01); *A61M 39/0247* (2013.01); *A61M 2025/0019* (2013.01); *A61M 2025/0056* (2013.01); *A61M 2039/0258* (2013.01)

(58) Field of Classification Search
CPC ....... A01N 37/44; A01N 37/00; A01N 37/02; A61K 31/20; A61K 31/727; A61K 45/06; A61L 29/14; A61L 29/16; A61L 2300/216; A61L 2300/404; A61M 25/0017; A61M 25/0045; A61M 39/0247; A61M 2025/0019; A61M 2025/0056; A61M 2039/0258
See application file for complete search history.

(56) References Cited

U.S. PATENT DOCUMENTS

| | | | |
|---|---|---|---|
| 4,164,496 | A | 8/1979 | Hao |
| 4,186,745 | A | 2/1980 | Lewis et al. |
| 4,343,788 | A | 8/1982 | Mustacich et al. |
| 4,392,848 | A | 7/1983 | Lucas et al. |
| 4,479,795 | A | 10/1984 | Mustacich et al. |
| 4,489,097 | A * | 12/1984 | Stone ............................ 514/558 |
| 4,767,400 | A | 8/1988 | Miller et al. |
| 4,968,306 | A | 11/1990 | Huss et al. |
| 5,077,281 | A | 12/1991 | Reinmuller |
| 5,364,650 | A | 11/1994 | Guthery |
| 5,436,008 | A | 7/1995 | Richter et al. |
| 5,688,516 | A * | 11/1997 | Raad et al. ..................... 424/409 |
| 5,913,856 | A | 6/1999 | Chia et al. |
| 6,166,007 | A * | 12/2000 | Sodemann ................. 514/222.5 |
| 6,949,087 | B2 | 9/2005 | VanTassel et al. |
| 6,958,049 | B1 | 10/2005 | Ash |
| 7,004,923 | B2 | 2/2006 | Deniega et al. |
| 9,072,296 | B2 * | 7/2015 | Mills et al. ..................... 424/409 |
| 2004/0116523 | A1 | 6/2004 | Popoff |
| 2005/0013836 | A1 | 1/2005 | Raad |
| 2006/0074388 | A1 | 4/2006 | Dextradeur et al. |
| 2006/0253101 | A1 | 11/2006 | Hartlep et al. |
| 2007/0281891 | A1 | 12/2007 | Wieslander |

FOREIGN PATENT DOCUMENTS

| | | |
|---|---|---|
| EP | 0083820 | 7/1983 |
| WO | WO2006099359 | 9/2006 |
| WO | WO2008089822 | 7/2008 |

OTHER PUBLICATIONS

Robert Shanks, et al, Catheter Lock Solutions Influence Staphylococcal Biofilm Formation on Abiotic Surfaces, 21 Nephrol. Dial Transplant. 2247 (2006).*
Stephen Ash, et al, Concentrated Sodium Citrate (23%) for Catheter Lock, 4 Hemodial. Int. 22 (2000).*
Albert Power, et al, Sodium Citrate Venous Heparin Catheter Locks for Cuffed Central Venous Catheters: A Single-Center Randomized Controlled Trial, 53 Am. J Kidney Dis. 1034 (2009).*

(Continued)

*Primary Examiner* — Sean Basquill
(74) *Attorney, Agent, or Firm* — Hall Estill Law Firm

(57) ABSTRACT

Microbial growth inhibiting solutions and methods of employing the microbial growth inhibiting solutions in flushing and coating medical devices are disclosed. In alternative embodiments, the microbial growth inhibiting solutions include combinations of a chelating agent with a $C_4$-$C_9$ carboxylate antimicrobial agent, for example, such as n-octanoic acid. Methods of using these microbial growth inhibiting solutions for coating a medical device and for inhibiting catheter infection are also disclosed.

60 Claims, 11 Drawing Sheets

(56) References Cited

OTHER PUBLICATIONS

Chirag Shah, et al, Antimicrobial Activity of a Novel Catheter Lock Solution, 46 Antimicrob. Agents Chemo. 1674 (2002).*

Harper and Epis; "Effect of chlorhexidine/EDTA/Tris against bacterial isolates from clinical specimens"; Microbios; vol. 51:107-112; 1987.

Said et al.; "Expression of H1 outer-membrane protein of Pseudomonas aeruginosa in relation to sensitivity to EDTA and polymyxin"; B.J. Med. Microbiol.; vol. 24:267-74; 1987.

Root et al.; "Inhibitory Effect of Disodium EDTA upon the Growth of Stapylococcus epidermidis in Vitro: Relation . . . "; Antimicrob Agents Chemother, vol. 32:1627-1631; 1988.

Ash et al.; "Concentrated Sodium Citrate (23%) for Catheter Lock"; Hemodialysis International; vol. 4:22-31; 2000.

BD Vacutainer (TM) Systems Brochure; 2002.

TauroLock (TM) Catalogue; Jun. 2011.

Dura-Lock-C (TM); Jan. 2012.

International Search Report for International Application No. PCT/US2011/049941; Jun. 1, 2012.

Written Opinion for International Application No. PCT/US2011/049941; Jun. 1, 2012.

Citralock (TM) Administration Manual; Nov. 23, 2012.

USP for Anticoagulant Sodium Citrate Solution; Dec. 1, 2012.

International Preliminary Report on Patentability for PCT/US2010/000905; Feb. 4, 2014.

* cited by examiner

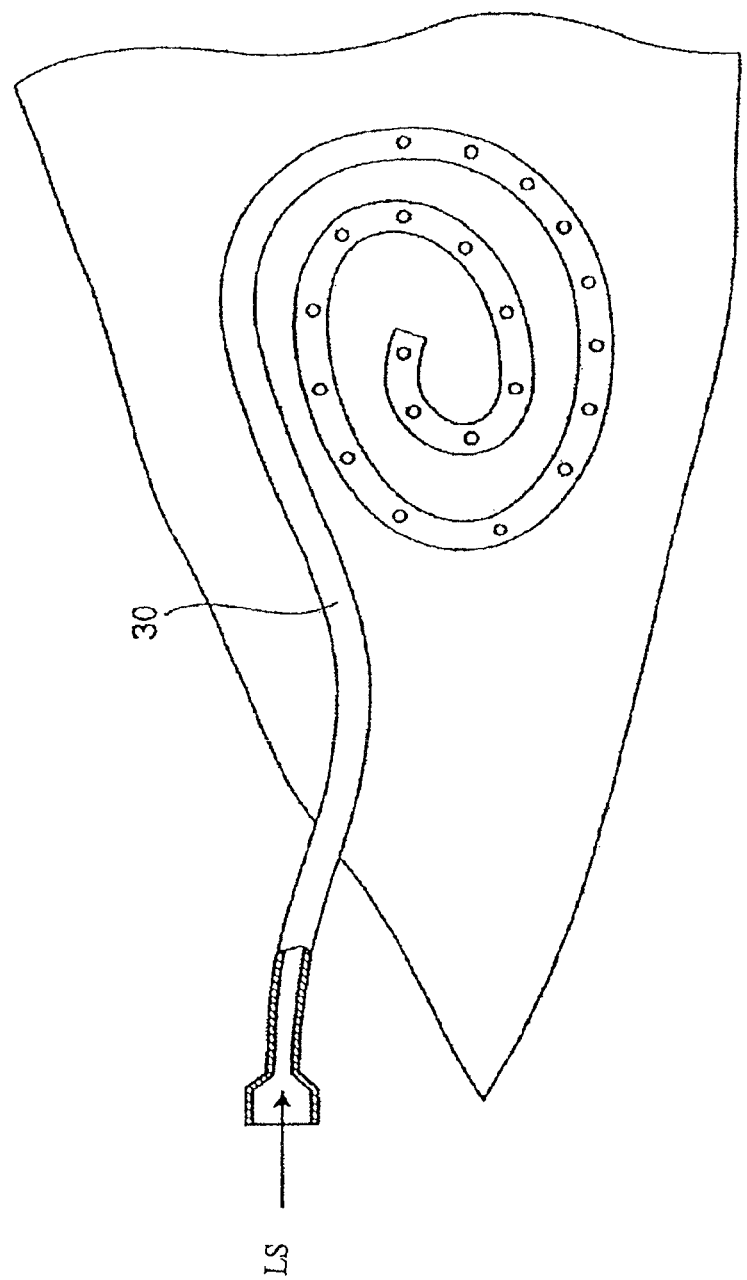

TRANSDERMAL VENOUS ACCESS LOCKING SOLUTIONS

PRIORITY CLAIM

This application is a continuation of patent application Ser. No. 13/222,221, filed on Aug. 31, 2011, which is a continuation-in-part of patent application Ser. No. 12/383,722, filed on Mar. 26, 2009, the entire disclosures of which are incorporated by reference.

FIELD

This invention relates to the field of transdermal indwelling medical devices, such as catheters, as well as to the field of microbial growth inhibiting solutions for flushing, locking and coating these medical devices. More specifically, the field of this invention relates to microbial growth inhibiting solutions. This invention also relates to microbial growth inhibiting solutions useful in maintaining catheter patency and preventing infection. Methods of using the microbial growth inhibiting solutions of the invention in the management and maintenance of transdermal vascular access catheters are also related to the present disclosure.

BACKGROUND

Transdermal medical devices, including vascular catheters, have become essential in the management of hospitalized or chronically ill patients. Unfortunately, vascular catheters have become the major source for hospital-acquired sepsis. Hence, the benefit derived from transdermal medical devices such as vascular catheters is often upset by infectious complications. Thrombotic occlusions of the lumen of central venous catheters ("CVC") are another complication that will often lead to the removal of catheters.

To reduce problems associated with thrombus formation, it is now common to "lock" intravascular access catheters between successive uses. Locking typically involves first flushing the catheter with saline to remove blood, medications, cellular debris and other substances from the catheter lumen. After the catheter has been flushed, a locking solution, typically heparin, is then injected to displace the saline and fill the lumen. The heparin locking solution both excludes blood from the lumen and actively inhibits clotting and thrombus formation within the lumen. To address infection, various antimicrobial substances have been combined with the locking solution in order to inhibit infection at the same time that thrombosis is being inhibited. However, problems with current and continuously emerging resistance to antimicrobial substances, as well as the over-use (and hence the increased risk of developing resistance) of antimicrobials, is an ever-growing concern.

*Staphylococcus epidermidis* and *S. aureus* account for 75% of CVC related infections. *Candida* species account for another 10% to 15% of such infections. The use of antistaphylococcal antibiotics to prevent these infections has been found to reduce CVC related bacterial infections, but only at the expense of the occurrence of higher rates of fungal (*Candida*) infections. The fibrous glycocalyx material produced by *Staphylococci* and *Candida* helps these organisms adhere and stick to catheter surfaces. These microbiological biofilm layers are made of fibrous glycocalyx material primarily polysaccharide in nature. The protective sheath provided by the glycocalyx at the infected site effectively prevents the elimination and treatment of these infections. As a result, microbial growth inhibiting solutions are needed that are effective for reducing or eliminating glycocalyx of infectious microorganisms typically associated with catheter colonization and infection.

Transdermal vascular catheters get engulfed by a fibrin sheath that subsequently acts to cover the internal and external surfaces of a catheter. This fibrin sheath provides such organisms as *Staphylococci* and *Candida*, with an enhanced adherence capacity to the catheter surface. Unlike these particular microbes, gram-negative bacilli do not adhere well to fibrin and fibronectin. A composition that halts fibrin formation would thus be particularly useful in halting the colonization of *Staphylococci*, *Candida*, and the like, at transdermal catheter sites.

Ethylenediaminetetraacetic acid ("EDTA") is an anticoagulant used in blood collection tubes. It is also recognized as a calcium chelating agent. EDTA is also recognized to have an antibacterial and antistaphylococcal effect (alone or in combination) (Harper & Epis (1987) *Microbios*. 51:107; Said et al. (1987) *J. Med. Microbiol*. 24:267; Root et al. (1988) *Antimicrob. Agents Chemother*. 32:1627). While those investigators found EDTA to be bacteriocidal, no remedy or suggestion of how the microbial glycocalyx of a device-related infection could be eliminated was provided.

Ethylene glycol tetraacetic acid ("EGTA") is another recognized chelating agent. This agent has not been described as antimicrobial. Triethylene tetramine dihydrochloride (trientine 2HCl) ("TTH") is a recognized chelating agent that chelates copper. TTH and other chelating agents, including diethylenetriamine pentaacetic acid ("DTPA"), are similarly not recognized as having antimicrobial activity.

Although glycopeptide antibiotics (vancomycin and teicoplanin) are effective against *staphylococci* in vitro and in tissue, they are not active against adherent *staphylococci* embedded in a biofilm layer, such as glycocalyx. While flushing with such agents may acutely destroy these microorganisms, the risk of rapid development of tolerant and resistant strains in the patient being treated makes this a contraindicated procedure in most cases.

U.S. Pat. No. 5,362,754 to Raad ("Raad I") describes compositions for use with catheters that include a tetracycline antibiotic, such as minocycline, and EDTA. Raad I teaches the use of 10-100 mg/ml of EDTA in combination with 0.001-100 mg/ml of minocycline and the more preferred combination of 20-60 mg/ml of EDTA and 2-9 mg/ml of minocycline. U.S. Pat. No. 5,688,516 also to Raad ("Raad II") in Example 10 teaches that minocycline and EDTA compositions of less than 3 mg/ml EDTA are ineffective at controlling all microbial growth. Raad II further teaches: "These studies also demonstrate the marked enhancement of anti-*Candida albicans* inhibitory activity where a ratio of minocycline to EDTA of 10:1 (10% EDTA) is used."

U.S. Pat. Nos. 4,343,788 and 4,479,795 to R. V. Mustacich describe polymer compositions containing carboxylate antimicrobial agents for incorporation into catheters. U.S. Pat. No. 4,392,848 to D. S. Lucas describes polymer compositions for incorporation into catheters that are permeable to carboxylate antimicrobial agents. U.S. Pat. No. 4,489,097 to R. L. Stone ("Stone") describes intravenous solutions containing carboxylate antimicrobial agents, preferably n-hexanoic and n-octanoic acids and pharmaceutically-acceptable, water-soluble salts thereof. Stone teaches the use of these carboxylate antimicrobial agents to sterilize intravenous solutions and to maintain these intravenous solutions sterile during manipulation. Administration of Stone's solutions as described into an intravenous catheter to "lock" the catheter under a static (no flow) situation would result in rapid occlusion of the access due to backflow of blood into the device and the lack of anticoagulation characteristics of the described compositions.

A prophylactic agent for catheter maintenance should both inhibit/eliminate the formation of polysaccharide-rich glycocalyx and eliminate *Staphylococci* and fungi. In view of the foregoing, there is a need for improved compositions, kits and methods for flushing, locking and disinfecting catheters. Such compositions should have antimicrobial activity against a broad spectrum of microorganisms, preferably including fungi and both gram-positive and gram-negative bacteria, and preferably be effective against planktonic (free-floating) and adherent microorganisms embedded in a biofilm. The compositions should discourage the development of resistant microbes, be relatively inexpensive, non-toxic, compatible with the catheter material, safe if inadvertently infused systemically, easy to implement, require minimum or no solution, and be useful with most or all types of implanted catheters, including hemodialysis and hemofiltration catheters, IV catheters, peritoneal dialysis catheters, urinary catheters, chemotherapy catheters, and the like. At least some of these objectives are met by embodiments of the invention described hereinafter.

SUMMARY

Embodiments of the present invention provide unique and effective microbial growth inhibiting solutions (e.g., locking solutions) that include effective amounts of a carboxylate antimicrobial agent, such as a $C_4$-$C_9$ carboxylate antimicrobial agent or antifungal agent, and a chelating agent. In one preferred embodiment, the chelating agent is EDTA and the $C_4$-$C_9$ carboxylate antimicrobial agent is n-octanoic acid. In other embodiments, the microbial growth inhibiting solutions comprise a $C_4$-$C_9$ carboxylate antimicrobial agent and a chelating agent other than EDTA. A preferred combination includes a $C_4$-$C_9$ carboxylate antimicrobial agent and a calcium chelating agent, such as EGTA. Chelating agents that may be used in conjunction with the present invention include, but are not limited to, EDTA, EGTA, DTPA, dimercaptosuccinic acid ("DMSA"), deferoxamine, dimercaprol, triethylene tetramine dihydrochloride, zinc citrate, combination of bismuth and citrate, penicillamine, etidronate and pharmaceutically acceptable salts thereof. Preferred chelating agents include those that chelate divalent metal cations such as Ca, Mg, Mn, Fe and Zn.

It has been surprisingly found that a $C_4$-$C_9$ carboxylate antimicrobial agent in combination with a chelating agent present in an amount of about 2 mg/mL, 1 mg/mL or lower can effectively inhibit microbial or fungal growth in a catheter. In any of the embodiments described herein, the microbial growth inhibiting solutions can include a combination of a chelating agent and a $C_4$-$C_9$ carboxylate antimicrobial agent, wherein the concentration of the chelating agent is present in an amount ranging from about 0.01 to about 2 mg/mL in the solution and the concentration of the antimicrobial agent is present in an amount ranging from about 0.05 mg/ml to about 5 mg/ml in the solution. In a preferred embodiment, the combination includes about 0.5 mg/ml of the chelating agent and about 1.15 mg/ml of the $C_4$-$C_9$ carboxylate antimicrobial agent.

Where n-octanoic acid is the antimicrobial agent of choice, it can be reconstituted to an appropriate concentration from a vial of n-octanoic acid and then combined in the manner described herein to provide a solution with the concentration of n-octanoic acid desired according to methods well known to those of ordinary skill in the art of microbial growth inhibiting solutions. The carrier solution, by way of example, can comprise saline, phosphate buffered saline, dextrose in water, Ringer's solution or water pH adjusted to 5.2 or less.

In an embodiment, the microbial growth inhibiting solutions include a pharmacologically acceptable carrier solution, such as water, Ringer's solution or saline pH adjusted to 5.2 or less. The microbial growth inhibiting solutions can have an in-use pH of about 6.0, or below, generally in the range of about 3.5 to about 5.8, or most preferably in the pH range of about 3.5 to about 5.2. Within this acidic pH range, proper concentrations of the carboxylate compounds in the free acid form quickly and efficiently kill a wide variety of bacteria and fungi.

In an embodiment, the chelating agents provide potent glycocalyx inhibiting potential. In addition, $C_4$-$C_9$ carboxylate antimicrobial agents of the compositions, such as n-octanoic acid at high concentrations, preferably have a fungicidal effect and a unique ability to penetrate a polysaccharide-rich glycocalyx biofilm layer. The combination of the $C_4$-$C_9$ carboxylate antimicrobial agent and chelating agent can advantageously provide anticoagulant, glycocalyx inhibiting, antibacterial and antifungal agent for the prevention of thrombogenesis, microbial adherence and device-related infections. N-octanoic acid in combination with EDTA is one example of such a combination that may be preferred for use in a kit. Chelating agents other than EDTA that are desired include EGTA and DTPA.

In another embodiment, methods of using microbial growth inhibiting solutions including the chelating agent with the $C_4$-$C_9$ carboxylate antimicrobial agent in a variety of therapeutic applications are provided. One such therapeutic application is for preventing catheter infections. An example of a composition to be used in the practice of these methods comprises n-octanoic acid together with a chelating agent. EDTA is an example of a chelating agent contemplated for use in these methods; however, other chelating agents would also be expected to be useful.

For use in maintaining catheter patency, the microbial growth inhibiting solutions may be efficaciously used with medical devices such as a central venous catheter, a peripheral intravenous catheter, an arterial catheter, a Swan-Ganz catheter, a hemodialysis catheter, an umbilical catheter, a percutaneous nontunneled silicone catheter, a cuffed tunneled central venous catheter, as well as with a subcutaneous central venous port.

Embodiments of the invention also provide medical devices, such as catheters, that are coated with any of the foregoing microbial growth inhibiting solutions. In one preferred embodiment, the microbial growth inhibiting solution comprises EDTA and n-octanoic acid. Where the chelating agent is other than EDTA, the microbial growth inhibiting solution in one example includes EGTA together with an antimicrobial agent such as n-octanoic acid. Particular exemplary medical devices that may be prepared and coated with the solutions of the present invention are provided in the above list.

Embodiments of the present invention also provide processes for preparing coated medical devices with the compositions described herein. In an embodiment, a process comprises exposing the medical device to a microbial growth inhibiting solution including a chelating agent combined with a $C_4$-$C_9$ carboxylate antimicrobial agent for a sufficient amount of time to provide a coating on the exposed surface of the device. Where the microbial growth inhibiting solution is in a liquid form, it can be allowed to dry on the device surface to form a film.

In a preferred embodiment of the above described processes, the device is first treated with a surfactant before exposing the device to the microbial growth inhibiting solution. Such surfactants, by way of example, include tridodecylmethyl ammonium chloride and benzalkonium chloride.

In another aspect, a catheter flushing solution is provided. Most preferably, the catheter flushing solution comprises a glycocalyx inhibiting concentration of a chelating agent and an effective amount of a $C_4$-$C_9$ carboxylate antimicrobial agent in a pharmaceutically acceptable carrier solution (e.g., saline pH adjusted to 5.2 or less).

In one preferred embodiment of the solution, the chelating agent is EGTA and the $C_4$-$C_9$ carboxylate antimicrobial agent is n-octanoic acid. Another embodiment of the catheter flushing solution includes about 0.5 mg/mL EDTA and about 1.15 mg/ml n-octanoic acid. By way of example, one carrier solution is saline, water, or a Ringer's solution pH adjusted to 5.2 or less. The catheter flushing solution may advantageously be used to inhibit the formation of polysaccharide-rich glycocalyx. In this manner, infections characterized by such a formation may be effectively eliminated.

Another aspect of the present invention provides a method of preparing a biofilm-resistant medical device. In one embodiment, the method comprises exposing a device with the microbial growth inhibiting solutions described herein. Any of a variety of catheters may be treated or coated according to the described method employing coating techniques well known to those of ordinary skill in the art.

While the method may be used to coat virtually any surface where glycocalyx formation is to be desirably inhibited, use of the method in preparing a microbial biofilm-resistant catheter device is particularly envisioned. By way of example, catheters that may be prepared and treated according to embodiments of the invention include a central venous catheter and a triple lumen catheter. It is anticipated that the method will provide a device resistant to polysaccharide-rich glycocalyx formation, such as that typical of *Staphylococci*.

In a preferred aspect of the described method, a biofilm-resistant medical device is prepared using a microbial growth inhibiting solution of a chelating agent and a $C_4$-$C_9$ carboxylate antimicrobial agent. An example of such solution comprises a combination of n-octanoic acid and EDTA, or a combination of a chelating agent other than EDTA together with a $C_4$-$C_9$ carboxylate antimicrobial agent. The various concentration ranges of the $C_4$-$C_9$ carboxylate antimicrobial agents and chelating agents described above are also contemplated as useful in the compositions for coating a medical device.

In one aspect, the method comprises preparing a microbial growth inhibiting solution of the desired combination in a biocompatible adherent coating carrier solution. The surface of the medical device of interest is then exposed to the microbial growth inhibiting solution for a period of time sufficient to allow the formation of a film or coating of the solution on the surface of the device. This may be accomplished, for example, by dipping the device in the solution. Most preferably, the device to be coated is a catheter. Such treatment provides a biofilm-resistant catheter.

Embodiments of the present invention also provide methods for inhibiting glycoprotein-rich glycocalyx formation at a catheter port. The method in one embodiment comprises flushing the catheter periodically with a microbial growth inhibiting solution comprising a glycocalyx-inhibiting concentration of a chelating agent and a $C_4$-$C_9$ carboxylate antimicrobial agent in a pharmacologically acceptable carrier solution.

The described methods can be used to inhibit infection at virtually any tunneled or untunneled catheter. As part of a catheter maintenance regimen, the catheter most preferably is to be flushed with a composition comprising a $C_4$-$C_9$ carboxylate antimicrobial agent and a chelating agent in a pharmaceutically acceptable carrier solution. The described regimen is repeated once a week, once every 4 days, once every 2 days, once a day (about every 24 hours), twice a day, every four hours or as needed according to patient needs.

In still another aspect, embodiments of the invention provide methods for eliminating microbial glycocalyx formation, particularly polysaccharide-rich (*Staphylococcal*) glycocalyx formation, at a catheter lumen. The method, in one embodiment, comprises preparing a microbial growth inhibiting solution comprising a chelating agent (e.g., EDTA, EGTA, or both) together with a $C_4$-$C_9$ carboxylate antimicrobial agent (e.g., n-butyric, n-pentanoic, n-hexanoic, n-heptanoic, n-octanoic or n-nonanoic acids and/or pharmaceutically acceptable salts thereof) in a carrier solution to provide a flushing composition, and flushing the catheter with an amount effective to inhibit microbial growth of the flushing composition.

Most preferably, the catheter will be flushed with a volume of about 3 mL of the described n-octanoic acid and EDTA solution containing about 0.5 mg/mL EDTA and about 1.15 mg/ml n-octanoic acid. The catheter can be flushed periodically at intervals of once a week, once every 4 days, once every 2 days, once a day, twice a day, every four hours, or as needed according to patient needs with about 2-3 mL of the n-octanoic acid and EDTA solution. The catheter flushing regimen may simply constitute once every time that the catheter is used or changed. In a preferred aspect of the method, the catheter is to be flushed at 4 hour intervals with the herein described solutions.

The compositions describe herein preferably remain therapeutically effective for use as a catheter-flushing agent after storage at a refrigerated temperature. However, the n-octanoic acid and EDTA solution should be brought to room temperature before use on an animal or patient.

The present invention in still another aspect provides a kit. In one embodiment, the kit comprises a container, such as a syringe, holding a volume of one of the foregoing solutions containing a $C_4$-$C_9$ carboxylate antimicrobial agent and a chelating agent and an implantable catheter lumen to receive the solution. The kit may further comprise a package, such as a box, tray, tube, envelope, pouch, or the like, for holding the container. The volume of the solution in the container is typically in the range from 1 mL-20 mL, preferably from 2 mL-10 mL, usually being about 2 mL-4 mL. Optionally, the container will usually comprise a syringe, or device to permit direct introduction of the solution into the indwelling catheter.

In another embodiment, the kit comprises a container, such as a compartmentalized syringe, that comprises a plurality of compartments. For example, the container can have three compartments, where one compartment comprises a $C_4$-$C_9$ carboxylate antimicrobial agent, such as n-octanoic acid; the second compartment comprises a chelating agent, such as EDTA; and the third compartment comprises a diluent, such as saline, Ringer's solution, or water pH adjusted to 5.2 or less. Kits that include a carrier adapted to receive at least two compartments constitute still another embodiment of the kit. In these embodiments, the chelating agent would be included together with the $C_4$-$C_9$ carboxylate antimicrobial agent within a compartment of the container. The second compartment would comprise a diluent, such as the ones described above. In an embodiment, the chelating agent and antimicrobial agent are included together in a first compartment of the device in dry powder form. The dry components would preferably be combined with the diluent of a second compartment to provide a solution suitable for use.

In these various embodiments, the kit preferably includes a chelating agent. In particular embodiments, the chelating agent is EDTA, and the $C_4$-$C_9$ carboxylate antimicrobial agent is, by way of example, n-octanoic acid.

In yet another aspect of the present invention, a method for disinfecting an implanted catheter is provided that includes introducing a solution comprising a $C_4$-$C_9$ carboxylate antimicrobial agent and a chelating agent in a pharmaceutically acceptable carrier solution into a lumen of a catheter where at least a portion of the catheter is sufficiently porous to permit diffusion of the solution outwardly from the lumen to the outer surface of the catheter and into the tissues or the bloodstream surrounding the catheter to inhibit infection. The implanted catheter may be a subcutaneous or transcutaneous indwelling catheter.

The ability to inhibit or prevent infection of the implanted catheter can be improved by utilizing catheters where at least a portion of the catheter body is sufficiently porous to allow the antimicrobial locking solution to permeate the catheter body and, preferably, pass outwardly (i.e., seep, ooze, leak, diffuse) into the tissue region surrounding the catheter. While the use of such porous or partially porous catheter bodies can be beneficial with many antimicrobial locking solutions, such as those taught in U.S. Pat. Nos. 4,186,745; 4,767,400; 4,968,306; 5,077,281; 5,913,856; 6,949,087; 7,004,923; and U.S. Patent Publication Nos. 2006/0074388 and 2006/0253101, it is particularly useful with the acids of the present invention. It will be appreciated that $C_4$-$C_9$ carboxylate antimicrobial agents have molecular weights and other qualities that enable them to readily penetrate into and through many porous materials. Exemplary porous materials for construction of the catheter body include silicone rubber, expanded PTFE (e.g., GORE-TEX®, medical membranes), TEFLON films, natural, regenerated or semi-synthetic cellulosic materials such as cellulose acetate, cellulose diacetate, cuprophane, and the like. Such materials may be formed into the tubular catheter bodies or may be incorporated as separate component(s) into the catheter bodies.

The described microbial growth inhibiting solutions are expected to be effective in preventing the adherence and colonization of catheter surfaces by *S. aureus, S. epidermidis,* and fungi, as well as effective in both treating and eliminating already formed glycocalyx formations of these infectious organisms.

It is contemplated that whenever appropriate, any embodiment of the present invention can be combined with one or more other embodiments of the present invention, even though the embodiments are described under different aspects or embodiments of the present invention. Additional features and advantages are described herein, and will be apparent from, the following Detailed Description and the figures.

BRIEF DESCRIPTION OF THE FIGURES

FIGS. 3A-3C illustrate methods according to the present invention for flushing, locking and disinfecting a peritoneal dialysis catheter.

DETAILED DESCRIPTION

Figure 1A:
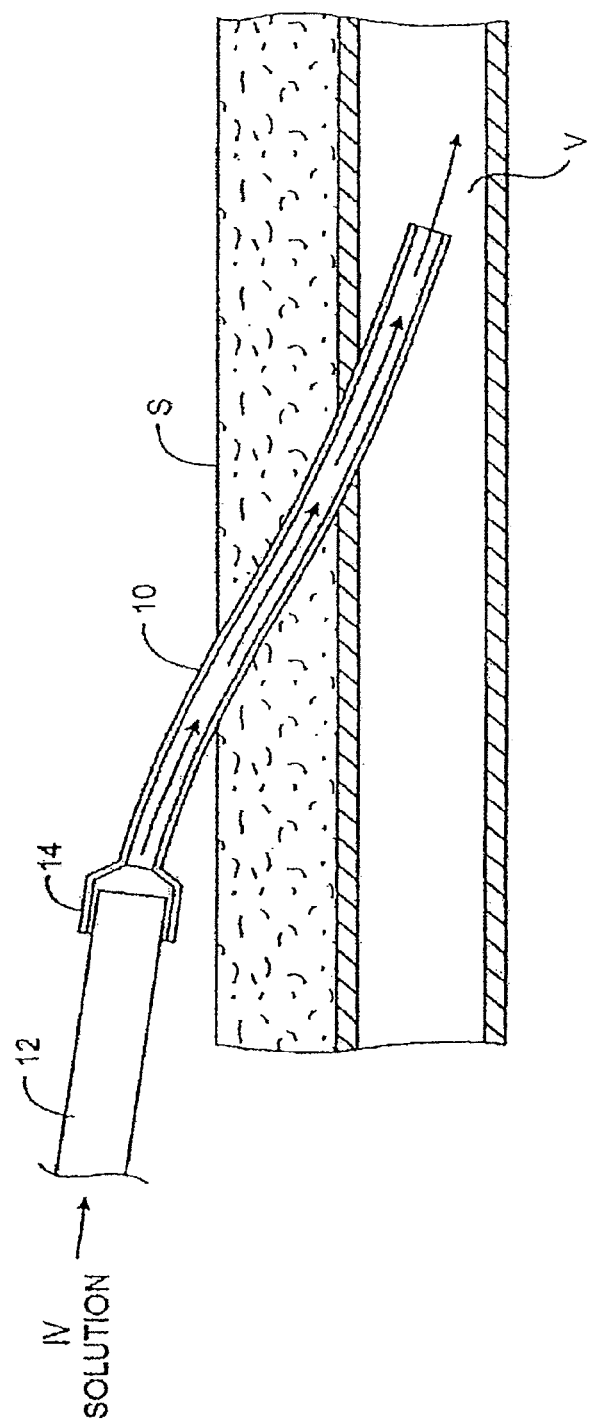
FIGS. 1A and 1B illustrate methods according to the present invention for locking and disinfecting a transcutaneous catheter.

The details of one or more embodiments of the invention are set forth in the accompanying description below. Although any methods and materials similar or equivalent to those described herein can be used in the practice or testing of the present invention, the methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

Definitions

The terms below have the following meanings unless indicated otherwise.

The term "biofilm" as used herein refers to a polysaccharide-rich glycocalyx that typically accompanies microbial surface colonization.

As used herein, a "biofilm-resistant" device or surface is a surface or device that will prevent the adherence or growth of organisms that produce polysaccharide-rich glycocalyx material. Such organisms include, but are not limited to, the *Staphylococcus aureus* and *S. epidermidis* species.

The term "glycocalyx inhibiting concentration" as used herein refers to a concentration effective to degrade, dissolve, or otherwise inhibit a polysaccharide-rich glycocalyx. By way of example, such a polysaccharide-rich glycocalyx is characteristic of established *staphylococcal* infections of *S. aureus* and *S. epidermidis*.

As used herein, the terms "implanted", "subdermal", "subcutaneous" and "indwelling" are used synonymously to refer to the placement of a medical device, for example, a catheter. These implanted catheters typically will have a distal end which is at least partially open to a body lumen. Most commonly, the catheters will be intravascular catheters where the distal end is implanted in or attached to a blood vessel—usually a vein, but in some cases an artery. Exemplary intravascular catheters include hemodialysis and hemofiltration catheters, as well as intravenous catheters. Intravenous catheters can be used for a wide variety of purposes, including fluid infusion and drug delivery. Catheters attached other than to the vasculature include peritoneal dialysis catheters which are open to the peritoneal cavity and urinary catheters which open to the bladder.

The medical devices, such as catheters, which are described herein may be transcutaneously implanted or subcutaneously implanted. By "transcutaneously implanted," it is meant that the distal end of the catheter is attached to or implanted within a target body lumen and a proximal end of the catheter is located externally to the patient. An intermediate portion of the catheter will thus pass through or penetrate the patient's skin, and the proximal end of the catheter will usually have a hub to permit selective attachment of infusion tubes, syringes, solution bags, and the like. Most commonly, the proximal attachment hub will have a luer fitting. By "subcutaneously implanted," it is meant that the entire catheter is implanted beneath the skin and no portion of the catheter extends through the skin. Such subcutaneously implanted catheters are typically attached to a fully implanted hub at their proximal ends. The hub permits percutaneous access via a needle or other penetrating element.

Embodiments of the present invention provide microbial growth inhibiting solutions of $C_4$-$C_9$ carboxylate antimicrobial agents in combination with chelating agents. These microbial growth inhibiting solutions are expected to be particularly useful in preventing the formation of the "biofilm" or polysaccharide-rich glycocalyx that typically accompanies microbial surface colonization. In particular, the microbial growth inhibiting solutions are expected to be most effective in breaking down *staphylococcal* glycocalyx and in inhibiting its formation. This feature renders the microbial growth inhibiting solutions of the present invention particularly useful in the treatment of *staphylococcal* infections where a polysaccharide-rich glycocalyx has formed or may potentially be formed, as well as in the prevention and treatment of *Staphylococcus* and *Candida* infection.

Embodiments of the present invention also provide treated or coated medical devices, such as catheters, that prevent *staphylococcal* or fungal colonization. The coating or film provided on these devices comprises a $C_4$-$C_9$ carboxylate antimicrobial agent, such as n-octanoic acid, and a chelating agent. A particular preferred combination of ingredients of the microbial growth inhibiting solutions includes n-octanoic acid and EDTA. Other preferred combinations comprise a glycocalyx inhibiting concentration or amount of a $C_4$-$C_9$ carboxylate antimicrobial agent and a chelating agent other than EDTA. Devices coated with these combinations of agents are also envisioned to be useful.

Antimicrobial Agents

The $C_4$-$C_9$ carboxylate antimicrobial agents used in any of the microbial growth inhibiting solutions and methods described herein can include non-aromatic water-soluble $C_4$-$C_9$ alkyl, alkenyl or alkynyl organic acids, or mixtures thereof, or any of their water-soluble, pharmaceutically-acceptable salts. Such salts include, for example, sodium, potassium and ammonium salts. The sodium and potassium salts are preferred.

While the various carboxylate compounds exhibit different degrees of antimicrobial activity (per mole), water-soluble agents having the formula: R—COOH, wherein R=$C_3$-$C_8$ n-alkyl, as well as pharmaceutically acceptable salts thereof or a combination thereof, exhibit excellent antimicrobial activity. The n-hexanoic and n-octanoic acids and pharmaceutically-acceptable, water-soluble salts thereof are much preferred, with n-octanoic acid being more preferred. These materials in their free acid form rapidly kill essentially all important gram positive and gram negative pathogens, and *Candida*, at low solution concentrations in the acid pH range.

The microbiocidal activity of the $C_4$-$C_9$ carboxylate antimicrobials is directly related to the presence of their respective free acids in solution. The concentration of free carboxylic acid in solution, as opposed to carboxylate salt (anionic) form, is a function of the solution pH. Carboxylic acid salts can be used, but only as long as the solution pH is such that a minimum lethal concentration ("MLC") of free acid is present. Accordingly, the amount of acid or acid salt used will vary somewhat with the use pH. The amount of a given acid salt or acid that will provide the MLC at a given pH will depend on the $pK_a$ of the acid. Of course, knowing the $pK_a$, the MLC of the particular acid and the use pH, the amount of any $C_4$-$C_9$ acid or acid salt to be used is easily calculated from the following formula:

$$pK_a = pH + \log([HC_x]/[C_{x-}]),$$

where $[HC_x]$ is the concentration of free acid of chain length x and $[C_{x-}]$ is the concentration of its anion.

In an embodiment, the antimicrobial agent is present in an amount ranging from about 0.05 mg/ml to about 5 mg/ml in the microbial growth inhibiting solution. More specifically, the amount of the antimicrobial agent can be about 0.05 mg/mL, 0.1 mg/mL, 0.25 mg/mL, 0.5 mg/mL, 0.75 mg/mL, 1 mg/mL, 1.25 mg/mL, 1.5 mg/mL, 1.25 mg/mL, 2 mg/mL, 2.25 mg/mL, 2.5 mg/mL, 2.75 mg/mL, 3 mg/mL, 3.25 mg/mL, 3.5 mg/mL, 3.75 mg/mL, 4 mg/mL, 4.25 mg/mL, 4.5 mg/mL, 4.75 mg/mL, 5 mg/mL and the like. It should be appreciated that any two amounts of the antimicrobial agent recited herein can further represent end points in a therapeutically preferred range of the antimicrobial agent. For example, the amounts of 0.5 mg/mL and 1.5 mg/mL can represent the individual amounts of the antimicrobial agent as well as a preferred range of the antimicrobial agent in the solution from about 0.5 mg/mL to about 1.5 mg/mL.

Chelating Agents and Buffers

In addition to the $C_4$-$C_9$ carboxylate antimicrobial agents, the microbial growth inhibiting solutions and methods described herein also include one or more chelating agents. Any of the microbial growth inhibiting solutions and methods described herein can also include one or more suitable buffers. Non-limiting examples of suitable chelating agents and buffers that can be used in various embodiments of the present invention can be selected from Tables 1 and 2, respectively. Pharmaceutically acceptable salts (e.g., edetate calcium disodium) of any chelating agents listed in Table 1 can also be used.

TABLE 1

| CHELATING AGENTS |
| --- |
| Deferoxamine |
| Dimercaprol |
| EDTA |
| EGTA |
| DTPA |
| DMSA |
| Penicillamine |
| Dimercaptosuccinic acid |

TABLE 2

| BUFFERING AGENTS |
| --- |
| Acetate-Acetic acid |
| Citrate-Citric acid |
| Phosphate-Phosphoric acid |
| Tartrate-Tartaric acid |
| Malate-Malic acid |
| Fumarate-Fumaric acid |
| Malonate-Malonic acid |
| Barbiturate-barbituric acid |

In certain preferred embodiments, the $C_4$-$C_9$ carboxylate antimicrobial agents are combined with EDTA. EDTA is available as calcium disodium EDTA and sodium EDTA formulations. A preferred form is sodium EDTA.

In alternative embodiments, the $C_4$-$C_9$ carboxylate antimicrobial agents are combined with chelating agents other than EDTA. Where administration of too much locking solution or administration of the locking solution too quickly would produce calcium complexation leading to hypocalcemia potentially resulting in ventricular arrhythmias and sudden death, use of such a chelating agent in high concentrations would be undesirable.

As will be appreciated by those of skill in the art, the foregoing lists are only intended to be exemplary. Other chelating agents, as well as buffers, are also expected to be useful and effective in combination with a $C_4$-$C_9$ carboxylate antimicrobial agent. These combinations formulated as a coating will preferably further include a material, such as a cationic surfactant (e.g., tridodecylmethyl ammonium chloride or benzalkonium chloride), that will enhance adherence or film forming characteristics, of the solution. As a solution for flushing or other medicinal use, the ingredients will be suspended in a carrier solution such as sterile saline, phosphate buffered saline, dextrose in water, Ringer's solution, distilled water or any other physiologically acceptable solution pH adjusted to 5.2 or less.

In an embodiment, the chelating agent is present in an amount ranging from about 0.01 mg/mL to about 2 mg/mL in the microbial growth inhibiting solution. More specifically, the amount of the chelating agent can be about 0.01 mg/mL, 0.05 mg/mL, 0.1 mg/mL, 0.15 mg/mL, 0.2 mg/mL, 0.25 mg/mL, 0.3 mg/mL, 0.35 mg/mL, 0.4 mg/mL, 0.45 mg/mL, 0.5 mg/mL, 0.55 mg/mL, 0.6 mg/mL, 0.65 mg/mL, 0.7 mg/mL, 0.75 mg/mL, 0.8 mg/mL, 0.85 mg/mL, 0.9 mg/mL, 0.95 mg/mL, 1 mg/mL, 1.05 mg/mL, 1.1 mg/mL, 1.15 mg/mL, 1.2 mg/mL, 1.25 mg/mL, 1.3 mg/mL, 1.35 mg/mL, 1.4 mg/mL, 1.45 mg/mL, 1.5 mg/mL, 1.55 mg/mL, 1.6 mg/mL, 1.65 mg/mL, 1.7 mg/mL, 1.75 mg/mL, 1.8 mg/mL, 1.85 mg/mL, 1.9 mg/mL, 1.95 mg/mL, 2 mg/mL and the like. It should be appreciated that any two amounts of the chelating agent recited herein can further represent end points in a therapeutically preferred range of the chelating agent. For example, the amounts of 0.2 mg/mL and 0.5 mg/mL can represent the individual amounts of the chelating agent as well as a preferred range of the chelating agent in the solution from about 0.2 mg/mL to about 0.5 mg/mL.

Methods of Flushing, Locking and Disinfecting a Catheter

Figure 1B:
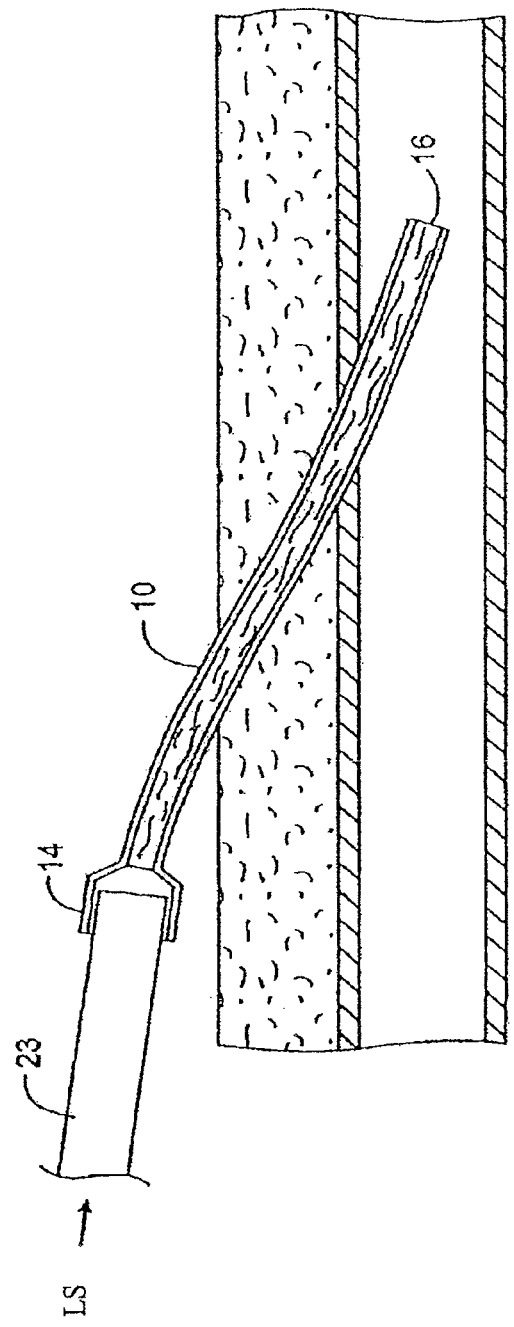

Referring now to FIGS. 1A and 1B, methods according to embodiments of the present invention for locking an implanted venous catheter 10 will be described. The venous catheter 10 will be implanted through a patient's skin S into a vein V for infusion of the patient. When it is desired to disconnect the patient from the source of infusion, it will be necessary to lock the catheter to inhibit plugging and fouling caused by coagulation, and preferably to further inhibit or eliminate the risk of infection. Shown in FIG. 1A, a tube 12 containing an IV solution will normally be connected to the proximal hub 14 of the catheter 10. The IV line 12 will be disconnected, and the catheter 10 rinsed with a flushing solution. After flushing is completed, a locking solution of a $C_4$-$C_9$ carboxylate antimicrobial agent and a chelating agent is introduced to fill the inner lumen of the catheter 10, as shown in FIG. 1B. Usually, a sufficient volume of the locking solution will be introduced to completely fill the lumen of the implanted catheter 10, with minimum excess passing from distal end 16 of the catheter. The loss of excess solution into a blood vessel or most other body lumens, however, will generally not be a problem. The "column" of the solution will then occupy the inner lumen, and the proximal hub will be sealed, helping retain the solution in place. The locking solution of a $C_4$-$C_9$ carboxylate antimicrobial agent and a chelating agent will effectively inhibit clotting and coagulation at the distal end 16 as well as inhibit or eliminate infection throughout the catheter. When it is desired to reattach the patient to the IV source, the solution will be removed and the catheter lumen flushed.

Figure 2A:
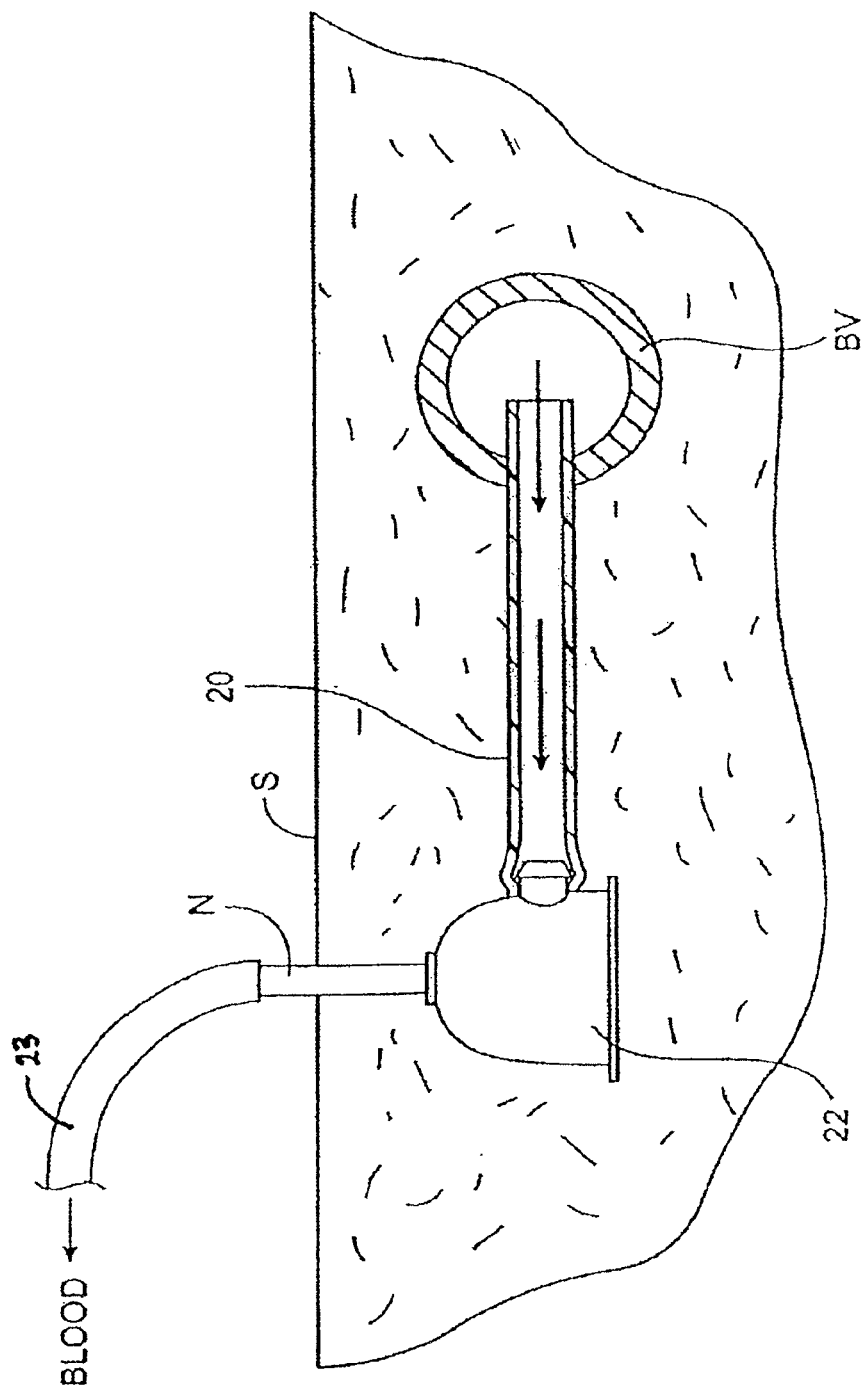
FIGS. 2A-2C illustrate methods according to the present invention for flushing, locking and disinfecting a subcutaneously implanted catheter.
Figure 2B:
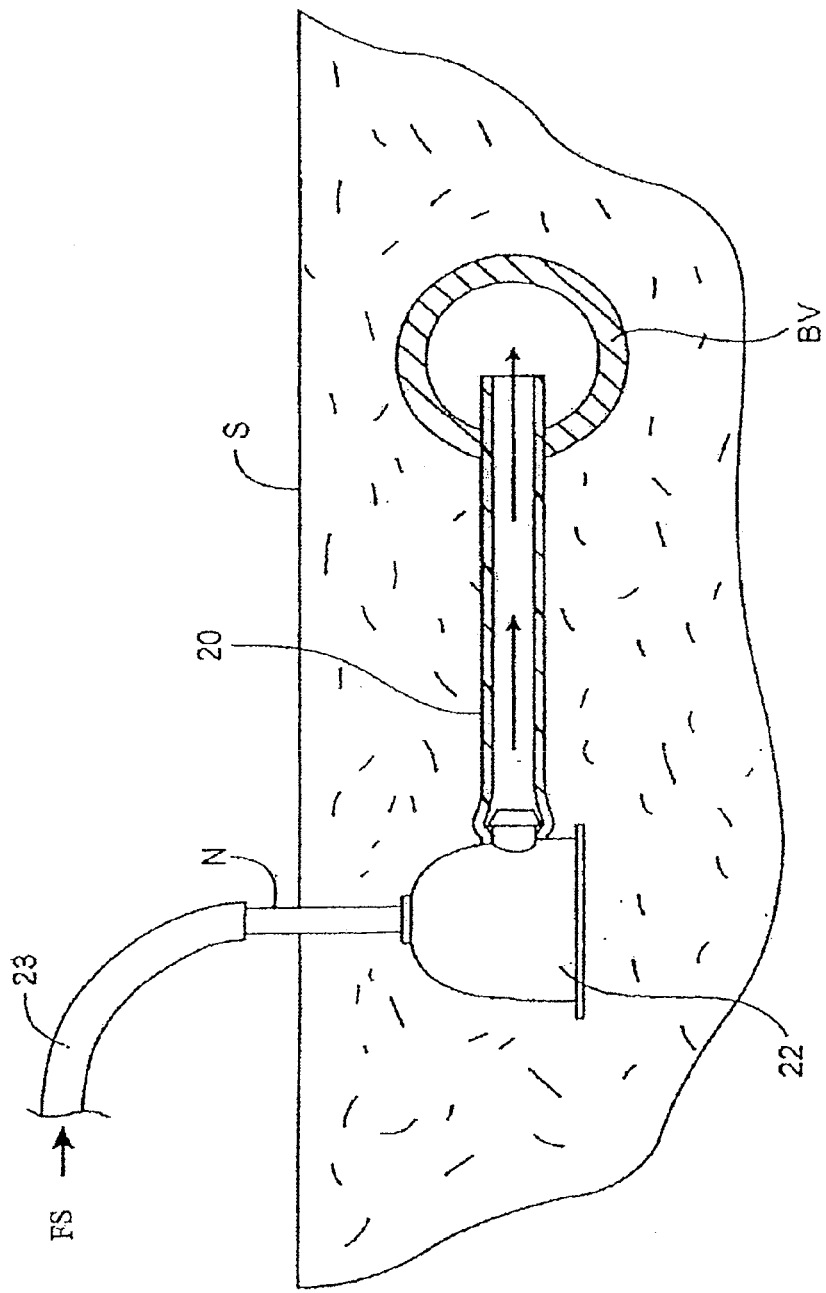
Figure 2C:
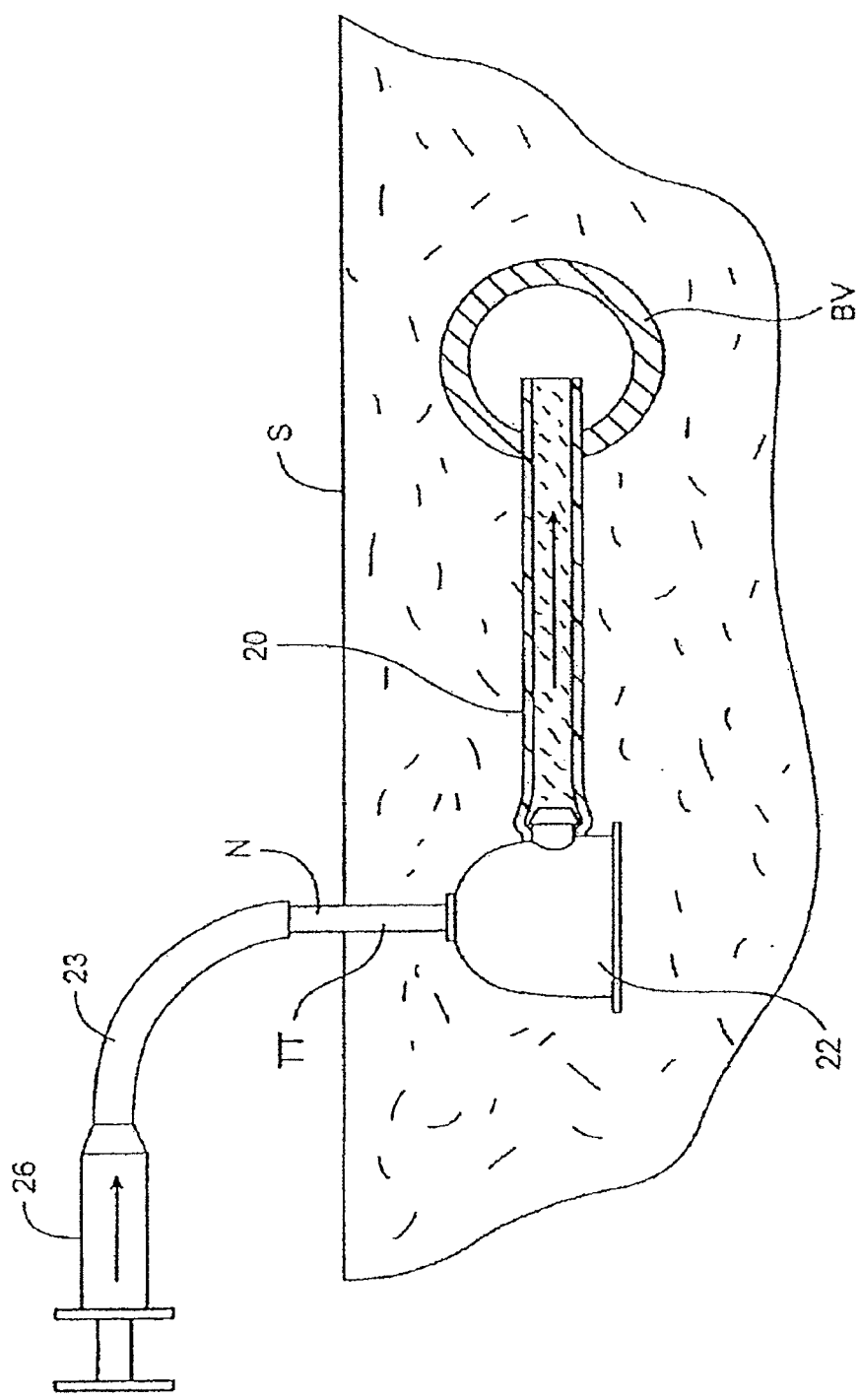

Referring now to FIGS. 2A-2C, flushing and locking of a subcutaneously implanted catheter 20 used for hemodialysis access will be described. The catheter 20 is implanted between a target blood vessel BV, typically a vein, and an implanted port 22. During hemodialysis, blood is withdrawn through the catheter 20, through the port 22 and externally through a needle N and connecting line 23 used to percutaneously access the port 22 (FIG. 2A). Alternatively, the port and catheter can used to return treated blood to the patient.

When it is desired to end a hemodialysis (or hemofiltration) treatment, a flushing solution ("FS") of a $C_4$-$C_9$ carboxylate antimicrobial agent and a chelating agent will be introduced through the needle N (typically from a syringe which is attached to the connecting line 23) to flush the lumen, as depicted in FIG. 2B. After the flush is complete, a locking solution is injected from a container such as a syringe 26 through the line 23/port 22 and into the lumen of catheter 20 to displace the flushing solution and lock the catheter (FIG. 2C). The locking solution will remain in place within the catheter 20. Alternatively or additionally, the locking solution can be a solution of a $C_4$-$C_9$ carboxylate antimicrobial agent and a chelating agent.

Figure 3A:
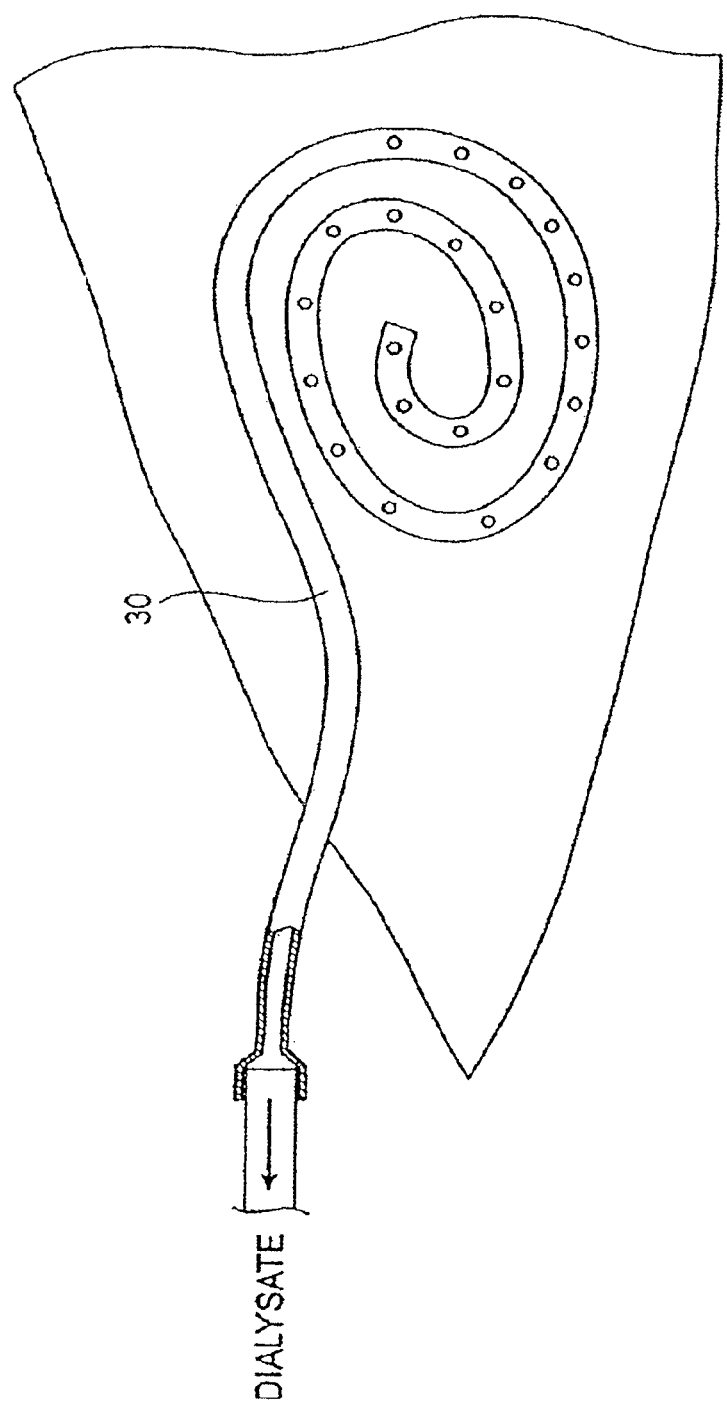
Figure 3B:
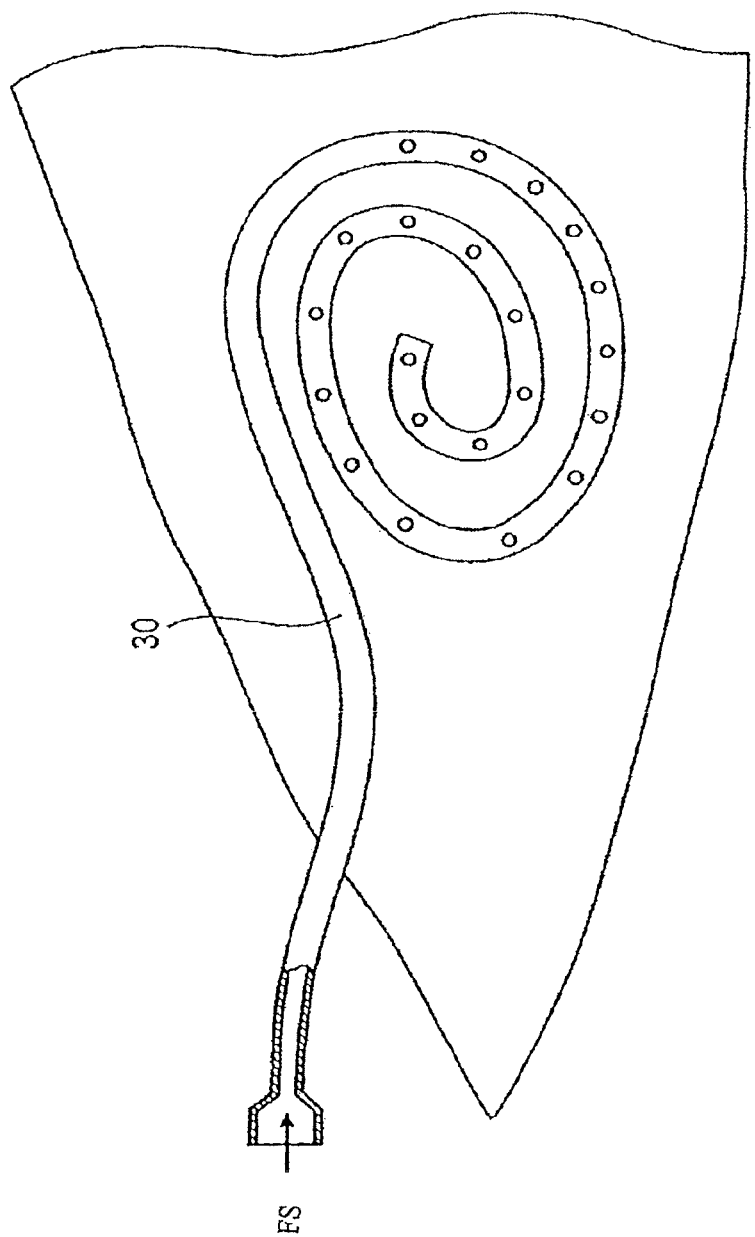

The methods of the present invention may also be used to flush and lock non-vascular catheters, such as peritoneal dialysis catheters 30, as shown in FIGS. 3A-3C. After a peritoneal dialysis treatment, the used dialysate is withdrawn from the catheter 30, as shown in FIG. 3A. After the dialysate has been sufficiently removed, the dialysis catheter 30 is flushed with a flushing solution FS of a $C_4$-$C_9$ carboxylate antimicrobial agent and a chelating agent, as shown in FIG. 3B. After flushing, the locking solution is introduced to the peritoneal dialysis catheter 30, as shown in FIG. 3C, so that it fills the lumen of the catheter, as described previously with the vascular catheters. Alternatively or additionally, the locking solution can be a solution of a $C_4$-$C_9$ carboxylate antimicrobial agent and a chelating agent.

Figure 4:
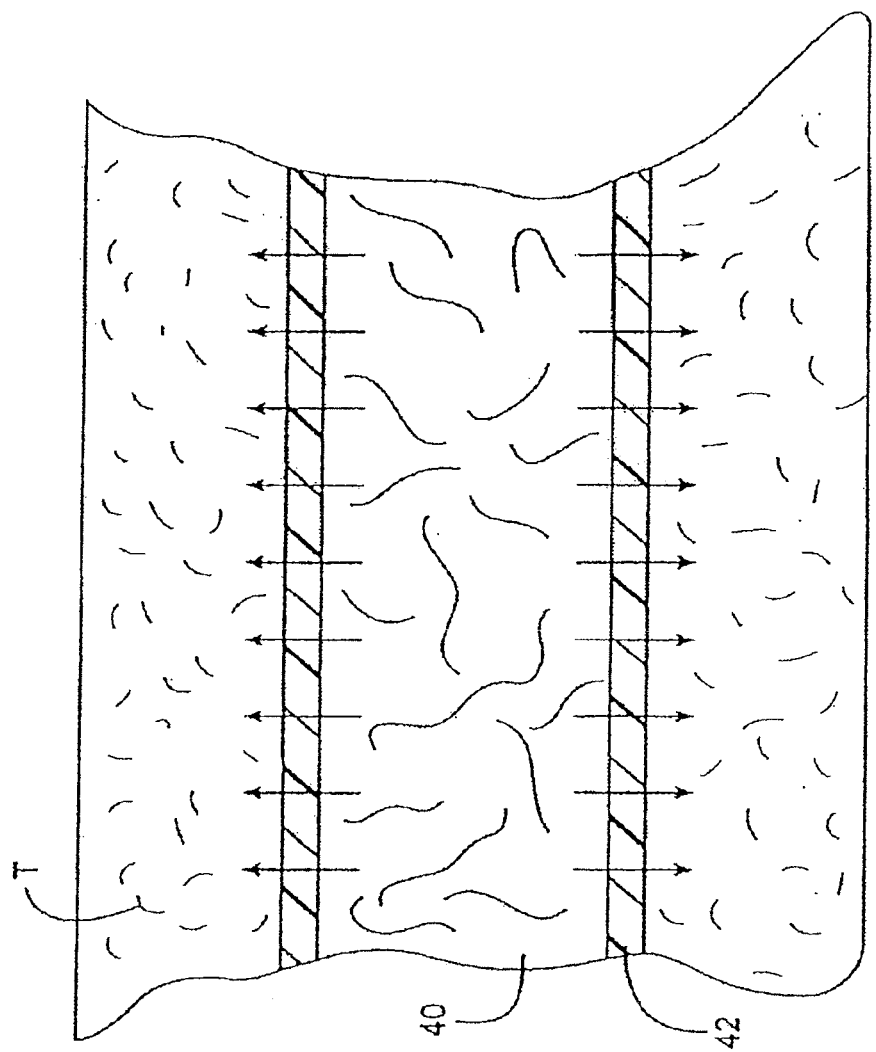
FIG. 4 illustrates an embodiment of the present invention where an antimicrobial locking solution permeates into an implanted catheter body and preferably into the tissue surrounding the catheter body.

Referring now to FIG. 4, the use of a locking solution containing a $C_4$-$C_9$ carboxylate antimicrobial agent and a chelating agent can be enhanced by utilizing an implanted catheter which is formed at least partly from a porous material. When the lumen 40 of the porous catheter body 42 is filled with a solution containing a $C_4$-$C_9$ carboxylate antimicrobial agent and a chelating agent, the solution will be able to slowly penetrate (i.e., seep) into the catheter body and outwardly into the tissue T surrounding the catheter, as shown by the arrows in FIG. 4. Thus, the antimicrobial properties of the locking solution will not be entirely limited to the interior lumen of the catheter, but will also be effective on the surface of the catheter and in the tissue region immediately surrounding the catheter body. Particularly suitable materials and porosity properties for the catheter bodies have been set forth above.

Figure 5:
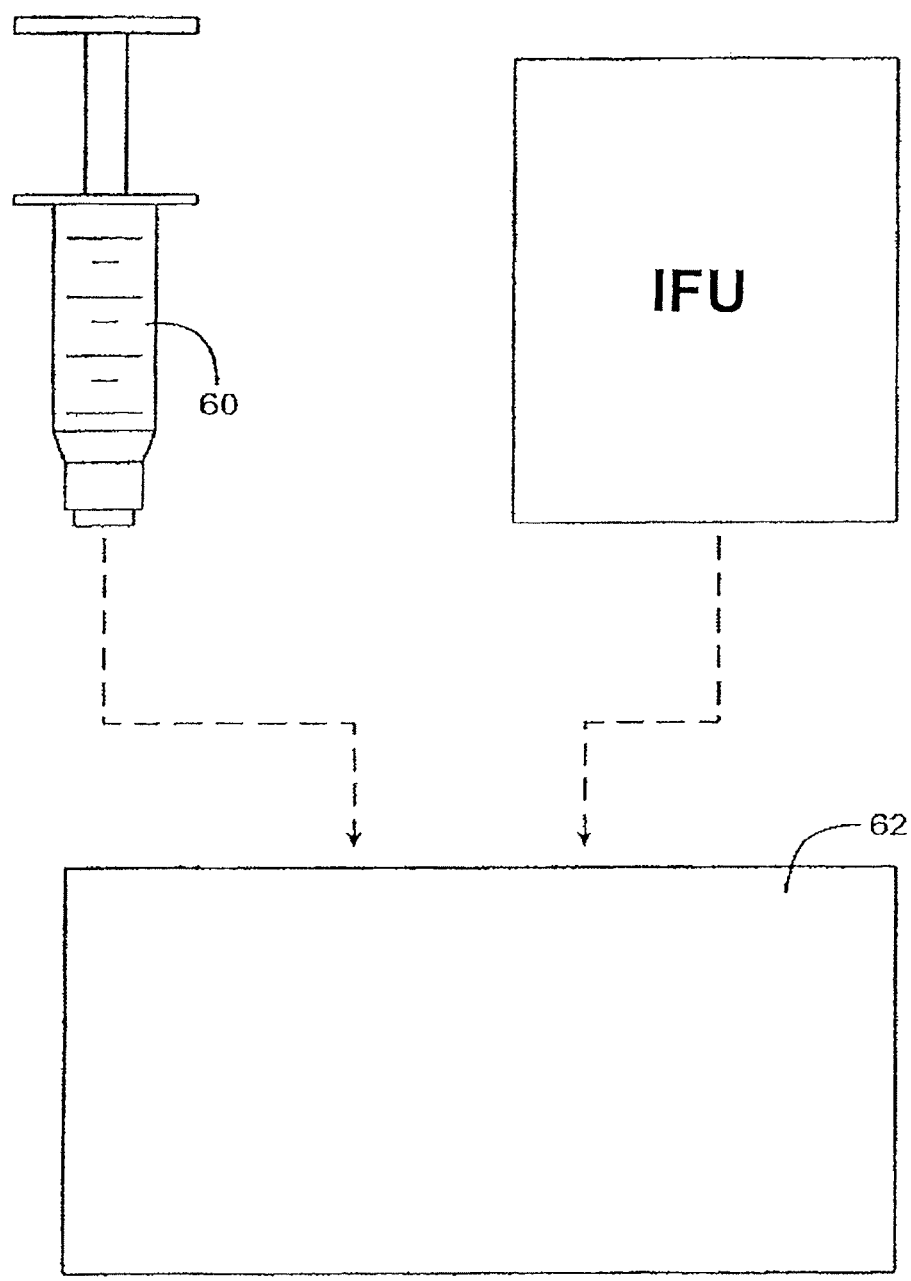
FIG. 5 illustrates a kit constructed in accordance with the principles of the present invention.

Referring now to FIG. 5, kits according to the present invention will include at least a container 60, such as a syringe, for holding a volume of a locking solution of a $C_4$-$C_9$ carboxylate antimicrobial agent and a chelating agent and an implantable catheter lumen to receive the solution. The volume will typically be within the ranges set forth herein. The kits can further contain a package 62 to hold the container 60. The package can be any conventional medical device package, including boxes, tubes, envelopes, trays and pouches. In addition, the kit can contain instructions for use ("IFU") setting forth a method for locking and/or disinfecting an implanted catheter by introducing the solution from the container into a lumen of the implantable catheter between successive uses of the catheter.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Evaluation of Microbial Growth Inhibiting Solutions

The following studies provided antimicrobial/antifungal testing of formulated microbial growth inhibiting solutions according to the present disclosure.

Methicillin-Resistant *Staphylococcus Aureus* ("MRSA")

A stock culture of *Staphylococcus aureus* was maintained as a frozen stock culture at −70° C. until use. The bacterial testing used *Staphylococcus aureus* isolated from human blood. A cell suspension was prepared from the frozen stock culture and cultivated in tryptic soy broth ("TSB") to yield approximately $1\times10^8$ colony forming units ("CFU") per milliliter for MRSA. The final concentration of the inoculum solution was confirmed using plate counts.

Bacterial testing—For the test, 9.9 ml of each test solution was inoculated with 100 ul of the MRSA cell suspension to yield a final cell concentration of approximately $1\times10^6$ CFU/ml. This represents a 1:100 dilution of the starting $1\times10^8$ CFU/ml culture; the initial cell concentration was calculated based on the inoculum plate count. Each test or control solution was evaluated in triplicate. Samples were collected at T=1 hour.

Sampling of treated organisms for growth—Each sample was serially diluted in PBS (pH 7.0) and plated in duplicate on tryptic soy agar ("TSA") plates. All plates were incubated inverted at 37° C. for 24 hours. For the remaining volume of the treated sample: 1) Each sample was filtered through a 0.22 μm filter membrane, and 2) Each filter was rinsed with 15 ml sterile water. The filter was placed directly onto a TSA plate and incubated without inversion for 24 hr at 37° C.

Analyses—The CFU/ml for each solution was logarithmically transformed (base 10). In cases where the plate counts were zero, a value of 0.5 was substituted for one of the zero counts. This substituted value was scaled, based on the dilution plated or volume filtered. The results of three experiments were averaged to determine the mean log density and the associated standard deviation was calculated. Log reductions were calculated for the cultures treated with locking solution by subtracting the mean log density at 24 hrs from that at time zero.

*Pseudomonas aeruginosa*

*Pseudomonas aeruginosa* (a representative gram negative bacterium) was grown to a defined log phase growth in culture. Representative samples of the culture were incubated/treated for a defined time with various vehicle (solvent) or locking solutions. Aliquots of the treated samples were plated on agar plates and colony counts performed after sufficient time for growth to assess the efficacy of the lock in killing the organisms of interest.

Bacterial strain and solution of cultures—A stock culture of *Pseudomonas aeruginosa* to be tested was maintained as a frozen stock culture at −70° C. until use. The bacterial testing used *Pseudomonas aeruginosa* isolated from human blood. A cell suspension was prepared from the frozen stock culture and cultivated in TSB to yield approximately $1\times10^8$ CFU per milliliter for *P. aeruginosa*. For reference, a 0.5 McFarland unit will typically reflect this approximate number of organisms. The final concentration of the inoculum solution was confirmed using plate counts.

Bacterial testing—For the test, 9.9 ml of each test solution was inoculated with 100 ul of the *P. aeruginosa* cell suspension to yield a final cell concentration of approximately $1\times10^6$ CFU/ml. Note that this represents a 1:100 dilution of the starting $1\times10^8$ CFU/ml culture. The initial cell concentration was calculated based on the inoculum plate count. Each test or control solution was evaluated in triplicate. Samples were collected at T=1 hour. Each sample was serially diluted in PBS (pH 7.0) and plated in duplicate on TSA plates. All plates were incubated inverted at 37° C. for 24 hours. For the remaining volume of the treated sample: 1) each sample was filtered through a 0.22 μm filter membrane, and 2) each filter was rinsed with 15 ml sterile water. The filter was placed directly onto a TSA plate and incubated (without inversion) for 24 hrs at 37° C.

Analyses—The CFU/ml for each solution was logarithmically transformed (base 10). In cases where the plate counts were zero, a value of 0.5 was substituted for one of the zero counts. This substituted value was scaled, based on the dilution plated or volume filtered. The results of three experiments were averaged to determine the mean log density and the associated standard deviation was calculated. Log reductions were calculated for the cultures treated with locking solution by subtracting the mean log density at 24 hrs from that at time zero.

*Candida albicans*

*Candida albicans* (a representative fungus/yeast) was grown to a defined log phase growth in culture. Representative samples of the culture were incubated/treated for a defined time with various vehicle (solvent) or locking solutions. Aliquots of the treated samples were plated on agar plates and colony counts performed after sufficient time for growth to assess the efficacy of the locking solution in killing the organisms of interest.

A stock culture of *Candida albicans* ATCC was maintained as a frozen stock culture at −70° C. until use. The bacterial testing used *Candida albicans* ATCC #90028 isolated from human blood. A cell suspension was prepared from the frozen stock culture and cultivated in TSB to yield approximately $1\times10^8$ CFU per milliliter for *C. albicans*. For reference, a 0.5 McFarland unit will typically reflect this approximate number of organisms. The final concentration of the inoculum solution was confirmed using plate counts.

Bacterial testing—For the test, 9.9 ml of each test solution was inoculated with 100 ul of the *C. albicans* cell suspension to yield a final cell concentration of approximately $1\times10^6$ CFU/ml. Note that this represents a 1:100 dilution of the starting $1\times10^8$ CFU/ml culture. The initial cell concentration was calculated based on the inoculum plate count. Each test or control solution was evaluated in triplicate. Samples were collected at T=1 hour.

Sampling of treated organisms for growth—Each sample was serially diluted in PBS (pH 7.0) and plated on TSA plates. All plates were plated in duplicate and incubated inverted at 37° C. for 24 hours. For the remaining volume of the treated sample: 1) each sample was filtered through a 0.22 μm filter membrane, and 2) each filter was rinsed with 15 ml sterile water. The filter was placed directly onto a TSA plate and incubated (without inversion) for 24 hr at 37° C.

Analyses—The CFU/ml for each solution was logarithmically transformed (base 10). In cases where the plate counts were zero, a value of 0.5 was substituted for one of the zero counts. This substituted value was scaled, based on the dilution plated or volume filtered. The results of three experiments were averaged to determine the mean log density and the associated standard deviation was calculated. Log reductions were calculated for the cultures treated with locking solution by subtracting the mean log density at 24 hrs from that at time zero. Table 3 shows the summary of results for study 1.0 discussed above.

TABLE 3

Summary of Study 1.0

| Solution | Disodium EDTA mg/mL | Citrate Buffer mM | Sodium Caprylate mg/mL | D5W 1/4 NS | Candida albicans ATCC #90028 CFU* | MRSA ATCC #700699 CFU* | Pseudomonas aeruginosa ATCC #27853 CFU* |
|---|---|---|---|---|---|---|---|
| 1 | 0.0625 | 1.5 | 0.071 | | TNTC | TNTC | 486 |
| 2 | 0.125 | 3 | 0.143 | | TNTC | TNTC | 50 |
| 3 | 0.25 | 6 | 0.287 | | TNTC | TNTC | 243 |
| 4 | | | | QS | TNTC | TNTC | TNTC |
| 5 | 0.5 | 12 | 0.575 | | 0 | 0 | 1 |
| 6 | 1.0 | 24 | 1.15 | | 0 | 40 | 0 |
| 7 | | 48 | | | TNTC | TNTC | 84 |
| Positive Control | | | | | $1.8 \times 10^7$ | $1.19 \times 10^8$ | $1.27 \times 10^8$ |

Final pH: 5.0
Reported values are average of three samples
*CFU: Colony forming units
TNTC: Too numerous to count

TABLE 4

Study 2.0 Concentration Summary

| Solution Final pH: 4.8 | Lot # | Disodium EDTA mg/mL | Citrate Buffer mM | Sodium Caprylate mg/mL |
|---|---|---|---|---|
| 1 | 0906301 | 0.5 | 25 | 0 |
| 2 | 0906302 | 0.5 | 25 | 1.15 |

TABLE 5

Summary of Study 2.0

| Solution | Staph aureus Antibiotic Sensitive ATCC #6538 CFU* | Staph epidermidis ATCC #12228 CFU* | Enterococcus fecalis VRE, Antibiotic Resistant ATCC #700802 CFU* | Escherichia coli ATCC #8739 CFU* | Klebsiella pneumoniae ATCC #BAA-1705 CFU* | Serratia marcescens ATCC #8100 CFU* |
|---|---|---|---|---|---|---|
| 1 | $7.3 \times 10^5$ | $4.5 \times 10^5$ | $1.9 \times 10^6$ | $1.58 \times 10^6$ | $7.0 \times 10^5$ | $3.3 \times 10^6$ |
| 2 | 0 | 0 | 0 | 0 | 13 | 0 |
| Positive Control | $2.9 \times 10^8$ | $1.2 \times 10^8$ | $2.9 \times 10^8$ | $1.4 \times 10^8$ | $1.1 \times 10^8$ | $2.9 \times 10^8$ |

Reported values are average of three samples
*CFU: Colony forming units
TNTC: To numerous to count The protocols for *Staphylococcus aureus, Staphylococcus epidermidis, Enterococcus fecalis VRE, Escherichia coli, Klebsiella pneumoniae*, and *Serratia marcescens* were similar or identical except for the microorganism tested. It is clear from study 1.0 that sodium caprylate at a concentration of 0.575 mg/mL and disodium EDTA at a concentration of 0.5 mg/mL pH adjusted to 5.0 with a citrate buffer was effective for a 7-8 log reduction of major medically important microorganisms. In addition, sodium caprylate and disodium EDTA at a concentration as low as 0.0625 mg/mL pH was effective for a 6-7 log reduction of at least one medically important microorganism (e.g., *Pseudomonas aeruginosa*). Overall, study 1.0 demonstrated that the microbial growth inhibiting solutions having a $C_4$-$C_9$ carboxylate antimicrobial agent and a chelating agent were synergistic at concentrations of 1 mg/mL chelating agent or lower.

As shown in Tables 4-5 (study 2.0), disodium EDTA in a citrate buffer at the reported concentration resulted in a 2 log reduction but was not capable of complete kill of the tested organisms. However, the addition of 1.15 mg/mL of sodium caprylate to the base disodium EDTA citrate buffer resulted in an 8 log reduction of test organisms.

Figure 6:
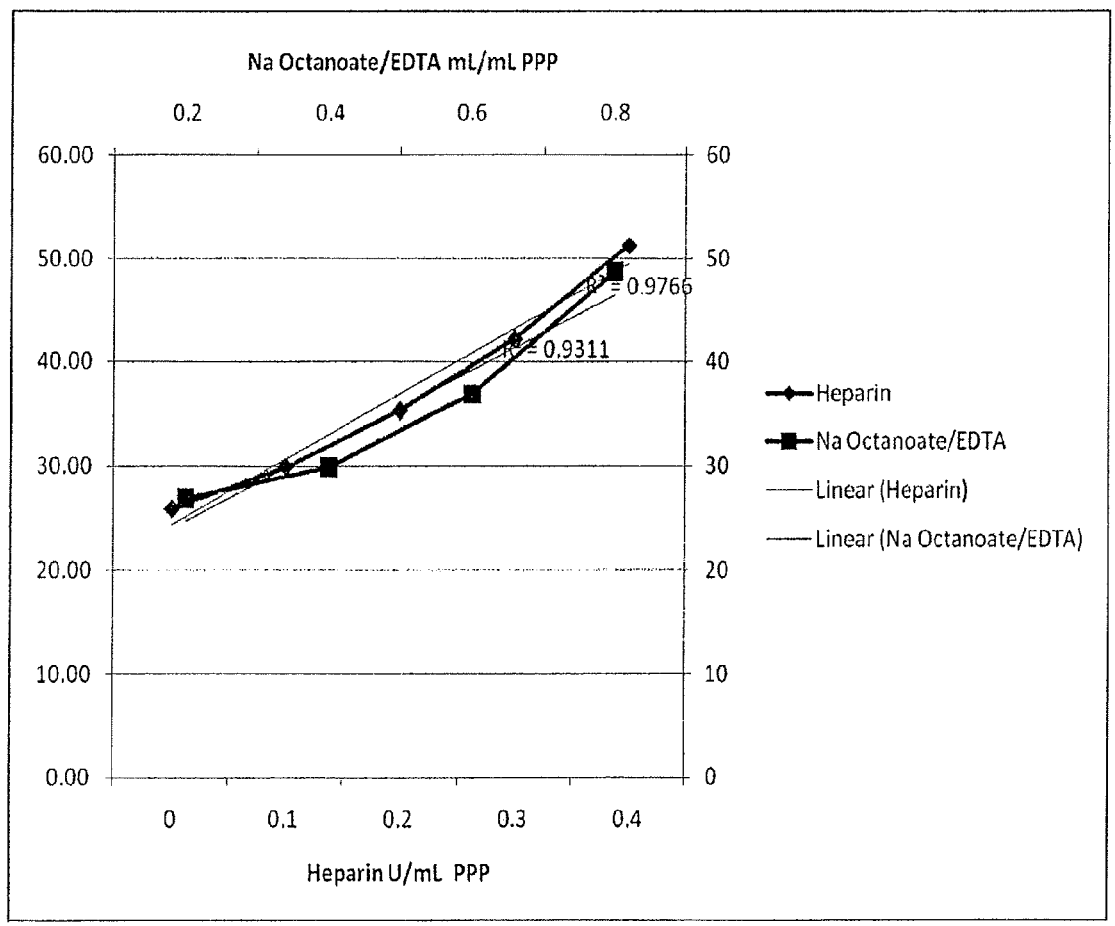
FIG. 6 shows a comparison of Na Octanoate/EDTA and Heparin by a PTT.

From studies 1.0 and 2.0, the effective concentrations of the chelating agent evaluated were well below previously reported concentrations and at a concentration that could greatly reduce the potential risk of sudden cardiac death associated at higher dosages. In addition, the evaluated microbial growth inhibiting solutions were capable of maintaining intravenous catheters in the "Locked" no flow state at the composition proposed as demonstrated in FIG. 6.

At concentrations of microorganisms one might expect to see in indwelling intravenous access devices, it was concluded that the microbial growth inhibiting solutions having concentrations of chelating agents according to the invention were capable of maintaining these devices and effectively reducing or eliminating the microorganisms as a source of systemic infection.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed:

1. A microbial growth inhibiting solution comprising a $C_4$-$C_9$ carboxylate antimicrobial agent and an agent that is a chelator and a buffer, wherein the $C_4$-$C_9$ carboxylate antimicrobial agent is present in an amount ranging from about 0.05 mg/mL to about 5 mg/mL, wherein the agent that is a chelator and a buffer is citrate and is present in an amount ranging from about 1 mg/mL to about 200 mg/mL, and wherein the solution has a pH of 5.2 or less.

2. The microbial growth inhibiting solution of claim 1 further comprising an additional chelating agent selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

3. The microbial growth inhibiting solution of claim 1, wherein the additional chelating agent chelates Ca, Mg, Mn, Fe or Zn.

4. The microbial growth inhibiting solution of claim 3, wherein the additional chelating agent is present in an amount ranging from about 0.1 mg/mL to about 2 mg/mL.

5. The microbial growth inhibiting solution of claim 3, wherein the additional chelating agent is present in an amount ranging from about 0.25 mg/mL to about 0.5 mg/mL.

6. The microbial growth inhibiting solution of claim 1, wherein the $C_4$-$C_9$ carboxylate antimicrobial agent is selected from the group consisting of:
agents having the formula R—COOH wherein R=$C_3$-$C_8$ n-alkyl, pharmaceutically acceptable salts thereof and combinations thereof.

7. The microbial growth inhibiting solution of claim 1, wherein the $C_4$-$C_9$ carboxylate antimicrobial agent is selected from the group consisting of n-butyric acid, n-pentanoic acid, n-hexanoic acid, n-heptanoic acid, n-octanoic acid, n-nonanoic acid, pharmaceutically acceptable salts thereof and combinations thereof.

8. The microbial growth inhibiting solution of claim 1 further comprising a pharmacologically acceptable carrier solution.

9. The microbial growth inhibiting solution of claim 8, wherein the pharmacologically acceptable carrier solution comprises saline, Ringer's solution, or water pH adjusted to 5.2 or less.

10. The microbial growth inhibiting solution of claim 1 further comprising an additional chelating agent present in an amount ranging from about 0.1 mg/mL to about 2 mg/mL wherein the $C_4$-$C_9$ carboxylate antimicrobial agent is present in an amount ranging from about 0.071 mg/mL to about 1.15 mg/mL.

11. The microbial growth inhibiting solution of claim 10, wherein the $C_4$-$C_9$ carboxylate antimicrobial agent comprises sodium caprylate, and the additional chelating agent comprises disodium ethylenediaminetetraacetic acid.

12. A method of disinfecting an implanted catheter from bacteria and fungi, the method comprising:
introducing to a lumen of a catheter a microbial growth inhibiting solution comprising a $C_4$-$C_9$ carboxylate antimicrobial agent and a chelating agent, wherein the $C_4$-$C_9$ carboxylate antimicrobial agent is present in an amount ranging from about 0.05 mg/mL to about 5 mg/mL and the chelating agent is present in an amount ranging from about 0.01 mg/mL to about 2 mg/mL.

13. The method of claim 12, wherein at least a portion of the catheter is sufficiently porous to permit diffusion of the solution outwardly from the lumen to the outer surface of the catheter and into tissues or the bloodstream surrounding the catheter to inhibit infection.

14. The method of claim 12, wherein the $C_4$-$C_9$ carboxylate antimicrobial agent is present in an amount ranging from about 0.05 mg/mL to about 5 mg/mL and is selected from the group consisting of:
agents having the formula R—COOH wherein R=$C_3$-$C_8$ n-alkyl, pharmaceutically acceptable salts thereof and combinations thereof.

15. The method of claim 12, wherein the $C_4$-$C_9$ carboxylate antimicrobial agent is selected from the group consisting of n-butyric acid, n-pentanoic acid, n-hexanoic acid, n-heptanoic acid, n-octanoic acid, n-nonanoic acid, pharmaceutically acceptable salts thereof and combinations thereof.

16. The method of claim 12, wherein the chelating agent is present in an amount ranging from about 0.1 mg/mL to about 1 mg/mL and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

17. The method of claim 12, wherein the chelating agent is present in an amount ranging from about 0.25 mg/mL to about 0.5 mg/mL and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

18. The method of claim 12, wherein the microbial growth inhibiting solution further comprises a buffer present in an amount ranging from about 1.5 to about 24 mM, wherein the $C_4$-$C_9$ carboxylate antimicrobial agent is present in an amount ranging from about 0.071 mg/mL to about 1.15 mg/mL, and the chelating agent is present in an amount ranging from about 0.0625 mg/mL to about 1 mg/mL.

19. The method of claim 18, wherein the $C_4$-$C_9$ carboxylate antimicrobial agent comprises sodium caprylate, the buffer comprises citrate, and the chelating agent comprises disodium ethylenediaminetetraacetic acid.

20. A method for coating a medical device, the method comprising:
exposing the medical device to a microbial growth inhibiting solution for a sufficient amount of time to provide a coating on the exposed surface of the device, wherein the microbial growth inhibiting solution comprises a $C_4$-$C_9$ carboxylate antimicrobial agent and a chelating agent, wherein the $C_4$-$C_9$ carboxylate antimicrobial agent is present in an amount ranging from about 0.05 mg/mL to about 5 mg/mL and the chelating agent is present in an amount ranging from about 0.01 mg/mL to about 2 mg/mL.

21. The method of claim 20 further comprising treating the device with a surfactant before exposing the device to the microbial growth inhibiting solution.

22. The method of claim 21, wherein the surfactant is selected from the group of surfactant consisting of tridodecylmethyl ammonium chloride, benzalkonium chloride and combinations thereof.

23. The method of claim 20, wherein the $C_4$-$C_9$ carboxylate antimicrobial agent is present in an amount ranging from about 0.05 mg/mL to about 5 mg/mL and is selected from the group consisting of:
agents having the formula R—COOH wherein R=$C_3$-$C_8$ n-alkyl, pharmaceutically acceptable salts thereof and combinations thereof.

24. The method of claim 20, wherein the $C_4$-$C_9$ carboxylate antimicrobial agent is selected from the group consisting of n-butyric acid, n-pentanoic acid, n-hexanoic acid, n-heptanoic acid, n-octanoic acid, n-nonanoic acid, pharmaceutically acceptable salts thereof and combinations thereof.

25. The method of claim 20, wherein the chelating agent is present in an amount ranging from about 0.1 mg/mL to about 1 mg/mL and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

26. The method of claim 20, wherein the chelating agent is present in an amount ranging from about 0.25 mg/mL to about 0.5 mg/mL and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

27. The method of claim 20, wherein the microbial growth inhibiting solution further comprises a buffer present in an amount ranging from about 1.5 to about 24 mM, wherein the $C_4$-$C_9$ carboxylate antimicrobial agent is present in an amount ranging from about 0.071 mg/mL to about 1.15 mg/mL, and the chelating agent is present in an amount ranging from about 0.0625 mg/mL to about 1 mg/mL.

28. The method of claim 27, wherein the $C_4$-$C_9$ carboxylate antimicrobial agent comprises sodium caprylate, the buffer comprises citrate, and the chelating agent comprises disodium ethylenediaminetetraacetic acid.

29. A medical device coated with a microbial growth inhibiting solution comprising a $C_4$-$C_9$ carboxylate antimicrobial agent and a chelating agent, wherein the $C_4$-$C_9$ carboxylate antimicrobial agent is present in an amount ranging from about 0.05 mg/mL to about 5 mg/mL and the chelating agent is present in an amount ranging from about 0.01 mg/mL to about 2 mg/mL.

30. The medical device of claim 29, wherein the medical device is selected from the group of devices consisting of a central venous catheter, a peripheral intravenous catheter, an arterial catheter, a Swant-Ganz catheter, a hemodialysis catheter, an umbilical catheter, a percutaneous nontunneled silicone catheter, a cuffed tunneled central venous catheter and a subcutaneous central venous pert.

31. The medical device of claim 29, wherein the $C_4$-$C_9$ carboxylate antimicrobial agent is present in an amount ranging from about 0.05 mg/mL to about 5 mg/mL and is selected from the group consisting of:
agents having the formula R—COOH wherein R=$C_3$-$C_8$ n-alkyl, pharmaceutically acceptable salts thereof and combinations thereof.

32. The medical device of claim 29, wherein the $C_4$-$C_9$ carboxylate antimicrobial agent is selected from the group consisting of n-butyric acid, n-pentanoic acid, n-hexanoic acid, n-heptanoic acid, n-octanoic acid, n-nonanoic acid, pharmaceutically acceptable salts thereof and combinations thereof.

33. The medical device of claim 29, wherein the chelating agent is present in an amount ranging from about 0.1 mg/mL to about 1 mg/mL and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

34. The medical device of claim 29, wherein the chelating agent is present in an amount ranging from about 0.25 mg/mL to about 0.5 mg/mL and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

35. The medical device of claim 29, wherein the microbial growth inhibiting solution further comprises a buffer present in an amount ranging from about 1.5 to about 24 mM, wherein the $C_4$-$C_9$ carboxylate antimicrobial agent is present in an amount ranging from about 0.071 mg/mL to about 1.15 mg/mL, and the chelating agent is present in an amount ranging from about 0.0625 mg/mL to about 1 mg/mL.

36. The medical device of claim 35, wherein the $C_4$-$C_9$ carboxylate antimicrobial agent comprises sodium caprylate, the buffer comprises citrate, and the chelating agent comprises disodium ethylenediaminetetraacetic acid.

37. A method for locking and/or flushing an implanted catheter, the method comprising:
filling a lumen of an implanted catheter open to a body lumen with a microbial growth inhibiting solution comprising a $C_4$-$C_9$ carboxylate antimicrobial agent and a chelating agent, wherein the $C_4$-$C_9$ carboxylate antimicrobial agent is present in an amount ranging from about 0.05 mg/mL to about 5 mg/mL and the chelating agent is present in an amount ranging from about 0.01 mg/mL to about 2 mg/mL.

38. The method of claim 37, wherein the $C_4$-$C_9$ carboxylate antimicrobial agent is present in an amount ranging from about 0.05 mg/mL to about 5 mg/mL and is selected from the group consisting of:
agents having the formula R—COOH wherein R=$C_3$-$C_8$ n-alkyl, pharmaceutically acceptable salts thereof and combinations thereof.

39. The method of claim 37, wherein the $C_4$-$C_9$ carboxylate antimicrobial agent is selected from the group consisting of n-butyric acid, n-pentanoic acid, n-hexanoic acid, n-heptanoic acid, n-octanoic acid, n-nonanoic acid, pharmaceutically acceptable salts thereof and combinations thereof.

40. The method of claim 37, wherein the chelating agent is present in an amount ranging from about 0.1 mg/mL to about 1 mg/mL and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

41. The method of claim 37, wherein the chelating agent is present in an amount ranging from about 0.25 mg/mL to about 0.5 mg/mL and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

42. The method of claim 37, wherein the microbial growth inhibiting solution further comprises a buffer present in an amount ranging from about 1.5 to about 24 mM, wherein the $C_4$-$C_9$ carboxylate antimicrobial agent is present in an amount ranging from about 0.071 mg/mL to about 1.15 mg/mL, and the chelating agent is present in an amount ranging from about 0.0625 mg/mL to about 1 mg/mL.

43. The method of claim 42, wherein the $C_4$-$C_9$ carboxylate antimicrobial agent comprises sodium caprylate, the buffer comprises citrate, and the chelating agent comprises disodium ethylenediaminetetraacetic acid.

44. A kit for locking and/or flushing an implanted catheter, the kit comprising:
a container holding a volume of a microbial growth inhibiting solution comprising a $C_4$-$C_9$ carboxylate antimicrobial agent and a chelating agent, wherein the $C_4$-$C_9$ carboxylate antimicrobial agent is present in an amount ranging from about 0.05 mg/mL to about 5 mg/mL and the chelating agent is present in an amount ranging from about 0.01 mg/mL to about 2 mg/mL; and
an implantable catheter lumen that receives the microbial growth inhibiting solution.

45. The kit of claim 44, wherein the container comprises a syringe.

46. The kit of claim 44, wherein the $C_4$-$C_9$ carboxylate antimicrobial agent is present in an amount ranging from about 0.05 mg/mL to about 5 mg/mL and is selected from the group consisting of:
agents having the formula R—COOH wherein R=$C_3$-$C_8$ n-alkyl, pharmaceutically acceptable salts thereof and combinations thereof.

47. The kit of claim 44, wherein the $C_4$-$C_9$ carboxylate antimicrobial agent is selected from the group consisting of n-butyric acid, n-pentanoic acid, n-hexanoic acid, n-heptanoic acid, n-octanoic acid, n-nonanoic acid, pharmaceutically acceptable salts thereof and combinations thereof.

48. The kit of claim 44, wherein the chelating agent is present in an amount ranging from about 0.1 mg/mL to about 1 mg/mL and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

49. The kit of claim 44, wherein the chelating agent is present in an amount ranging from about 0.25 mg/mL to about 0.5 mg/mL and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

50. The kit of claim 44, wherein the microbial growth inhibiting solution further comprises a buffer present in an amount ranging from about 1.5 to about 24 mM, wherein the $C_4$-$C_9$ carboxylate antimicrobial agent is present in an amount ranging from about 0.5 mM to about 8 mM, and the chelating agent is present in an amount ranging from about 0.0625 mg/mL to about 1 mg/mL.

51. The kit of claim 50, wherein the $C_4$-$C_9$ carboxylate antimicrobial agent comprises sodium caprylate, the buffer comprises citrate, and the chelating agent comprises disodium ethylenediaminetetraacetic acid.

52. A kit for locking and/or flushing an implanted catheter, the kit comprising:
a container having a first compartment holding a $C_4$-$C_9$ carboxylate antimicrobial agent and a chelating agent in powder form and a second compartment holding a pharmacologically acceptable carrier solution, wherein the $C_4$-$C_9$ carboxylate antimicrobial agent is present in an amount ranging from about 0.05 mg/mL to about 5 mg/mL and the chelating agent is present in an amount ranging from about 0.01 mg/mL to about 2 mg/mL when mixed with the pharmacologically acceptable carrier solution.

53. The kit of claim 52, wherein the container comprises an implantable catheter lumen.

54. The kit of claim 52, wherein the container comprises a syringe.

55. The kit of claim 52, wherein the $C_4$-$C_9$ carboxylate antimicrobial agent is present in an amount ranging from about 0.05 mg/mL to about 5 mg/mL when mixed with the pharmacologically acceptable carrier solution and is selected from the group consisting of:

agents having the formula R—COOH wherein R=$C_3$-$C_8$ n-alkyl, pharmaceutically acceptable salts thereof and combinations thereof.

56. The kit of claim 52, wherein the $C_4$-$C_9$ carboxylate antimicrobial agent is selected from the group consisting of n-butyric acid, n-pentanoic acid, n-hexanoic acid, n-heptanoic acid, n-octanoic acid, n-nonanoic acid, pharmaceutically acceptable salts thereof and combinations thereof.

57. The kit of claim 52, wherein the chelating agent is present in an amount ranging from about 0.1 mg/mL to about 1 mg/mL when mixed with the pharmacologically acceptable carrier solution and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

58. The kit of claim 52, wherein the chelating agent is present in an amount ranging from about 0.25 mg/mL to about 0.5 mg/mL when mixed with the pharmacologically acceptable carrier solution and is selected from the group consisting of ethylenediaminetetraacetic acid, diethylenetriamine pentaacetic acid, ethylene glycol tetraacetic acid, etidronate, dimercaptosuccinic acid, deferoxamine, dimercaprol, triethylene tetramine dihydrochloride, zinc citrate, combination of bismuth and citrate, penicillamine, pharmaceutically acceptable salts thereof and combinations thereof.

59. The kit of claim 52, wherein first compartment or the second compartment further comprises a buffer present in an amount ranging from about 1.5 to about 24 mM, wherein the $C_4$-$C_9$ carboxylate antimicrobial agent is present in an amount ranging from about 0.071 mg/mL to about 1.15 mg/mL, and the chelating agent is present in an amount ranging from about 0.0625 mg/mL to about 1 mg/mL when mixed with the pharmacologically acceptable carrier solution.

60. The kit of claim 59, wherein the $C_4$-$C_9$ carboxylate antimicrobial agent comprises sodium caprylate, the buffer comprises citrate, and the chelating agent comprises disodium ethylenediaminetetraacetic acid.

* * * * *